United States Patent [19]
Tryggvason et al.

[11] Patent Number: 6,063,901
[45] Date of Patent: May 16, 2000

[54] MACROPHAGE RECEPTOR WITH A COLLAGENOUS DOMAIN

[76] Inventors: Karl Tryggvason, Fyysinkontie 8, SF-90570 Oulu; Outi Elomaa, Asemakatu 41, 90100 Oulu; Maarit Kangas, Sipolankuja 4, 90800 Oulu, all of Finland

[21] Appl. No.: 08/893,467

[22] Filed: Jul. 11, 1997

Related U.S. Application Data

[62] Division of application No. 08/392,367, Feb. 21, 1995, Pat. No. 5,691,197.
[51] Int. Cl.⁷ .................................................. C07K 14/705
[52] U.S. Cl. .............................................. 530/350; 930/10
[58] Field of Search ................................ 530/350; 930/10

[56] References Cited

PUBLICATIONS

Asheknas et al. "Structures and High and Low Affinity Ligand Binding Properties of Murine Type I and Type II Macrophage Scavenger Receptors"; *Journal of Lipid Research*; vol. 34, pp. 983–1000; 1993.

Krieger & Herz *Ann. Rev. Biochem.*; vol. 63, pp. 601–637; 1994.

*Primary Examiner*—Anthony C Caputa
*Assistant Examiner*—Robert C. Hayes
*Attorney, Agent, or Firm*—Fay, Sharpe, Fagan, Minnich & McKee

[57] ABSTRACT

The present invention is directed to processes for isolating and identifying the nucleotide sequence of a gene for a novel macrophage receptor with collagenous structure, termed "MARCO". The new macrophage receptor with a collagenous domain binds gram positive and negative bacteria and acetylated LDL. Moreover, the invention relates to the nucleotide sequence for MARCO identified by the process of the invention and the isolated and purified polypeptide chain encoded by such a sequence.

5 Claims, 12 Drawing Sheets

(6 of 12 Drawing Sheet(s) Filed in Color)

Figure 2A

```
 811 TCCCCTGGAGCTCAGGGAGGTAAAGGTGATGCTGGAAAACCAGGCCTACCAGGTTTGGCTGGATCTCCAGGAGTCAAAGGTGACCAAGGA
 271  S  P  G  A  Q  G  G  K  G  D  A  G  K  P  G  L  P  G  L  A  G  S  P  G  V  K  G  D  Q  G

901 AAACCTGGAGTGCAGGGTGTTCCAGGCCCTCAAGGTGCACCAGGACTTTCAGTGCCAAGGTGAGCCAGGACGCACTGGTCTTCCTGGG
 301  K  P  G  V  Q  G  V  P  G  P  Q  G  A  P  G  L  S  G  A  K  G  E  P  G  R  T  G  L  P  G

991 CCAGCAGGACCCCCGGGAATTGCTGGGAATCCAGGGTGTGAAAGGAAGCAAGGGTGACACAGGAATTCAAGGACAGAAAGGC
 331  P  A  G  P  P  G  I  A  G  N  P  G  I  A  G  V  K  G  S  K  G  D  T  G  I  Q  G  Q  K  G

1081 ACAAAGGAGAATCAGGAGTCCCAGGTCTTGTAGGCAGAAAGGGAGACACTGGAAGCCCTGGGCTGGCAGGTCCCAAAGGAGAACCTGGA
 361  T  K  G  E  S  G  V  P  G  L  V  G  R  K  G  D  T  G  S  P  G  L  A  G  P  K  G  E  P  G

1171 CGAGTCGGTCAGAAGGGAGACCCGGGATGAAAGGGAGACCCGGGATGAAATGAAGGGGGATGAAAGGGCGAATCTTTC
 391  R  V  G  Q  K  G  D  P  G  M  K  G  S  S  G  Q  Q  G  E  K  G  Q  K  G  E  S  F

1261 CAACGCGTCCGATCATGGGTGGCACCAACAGAGCCGAAGTTTACTATAACAATGAGTGGGGACAATTTGTⒸGATGATGATTGG
 421  Q  R  V  R  I  M  G  G  T  N  R  G  R  A  E  V  Y  Y  N  N  E  W  G  T  I Ⓒ D  D  D  W

1351 GATAATAATGATGCGACTGTCTTCⒸCGGATGCTAGCAGCTATGGAGGTGGCTCTGGAAGCAACATC
 451  D  N  N  D  A  T  V  F Ⓒ R  M  L  G  Y  S  R  G  R  A  L  S  S  Y  G  G  G  S  G  N  I

1441 TGGCTGGACAATGTGAATTGTGGGGCACAGAGAACAGTTTGTGGACTGCAGTAAGAACTCCTGGGCAATCACAATTGCGTACATAAT
 481  W  L  D  N  V  N Ⓒ R  G  T  E  N  S  L  W  D Ⓒ S  K  N  S  W  G  N  H  N Ⓒ V  H  N

1531 GAAGATGCGGGTGTGGAAGTCCTGACTTGGGAGCCCGAGAGGTCATCAGTGTGTCCCCAGGTGTCTTTGGTTCCACCCACATGAAAT
 511  E  D  A  G  V  E Ⓒ S ter 1621 CTGTGGGCTTGCCAACTCTGTTGAGGGAAGTTAATAAAGCTCAAGTGGGATCTGAAAAAAAAAAAAAAAAAAAAAAAAAAA
```

Figure 2B

MACROPHAGE RECEPTOR WITH A COLLAGENOUS DOMAIN

This is a divisional of application Ser. No. 08/392,367 filed on Feb. 21, 1995, now U.S. Pat. No. 5,691,197.

FIELD OF THE INVENTION

The present invention is directed to a method for isolating and identifying the nucleotide sequence for a novel macrophage receptor with a collagenous domain, termed "MARCO". In addition, the invention relates to the nucleotide sequence for MARCO identified by the process of the invention and the isolated and purified polypeptide chain encoded by such a nucleotide sequence. The invention also provides for the use of the identified nucleotide sequence (or fragments thereof) to detect the gene or its parts, or its mRNA transcript in tissue, cell or fluid samples in normal or pathological situations. Moreover, the invention relates to the production of MARCO as recombinant protein or purified from tissues as well as for the generation of antibodies against the protein itself, and for the use of such antibodies to detect the protein in tissue, cell or fluid samples, or to interfere with the function of the receptor.

BACKGROUND OF THE INVENTION

Macrophages are bone marrow-derived cells that form an important part of the host defense system. They play a role in physiological as well as pathological processes, such as inflammation, fibrosis atherogenesis, and tumor invasion.

Macrophages are relatively large (10–20 µm), long-lived, amoeboid, phagocytic and pinocytotic cells present in blood, lymph and other tissues. They are derived from monocytes which form a pool of precursors migrating from blood into peripheral tissues such as liver, spleen, lung, lymph nodes, peritoneum, skin, brain and bone, where they differentiate into macrophages with organ specific features. Macrophages play important roles in host resistance to a variety of pathogenic microorganisms, having important functions in, for example, phagocytosis, inflammation, antibody formation, cell-mediated cytotoxicity and delayed hypersensitivity.

In this regard, the major characteristic of macrophages is their ability to recognize, internalize and destroy a variety of foreign and endogenous substances and, thus, to function as scavengers that engulf pathogenic organisms, such as bacteria, parasites and viruses. Macrophages also remove extravasated blood cells or dead cells in tissues and, thereby, participate in the maintenance of tissues. Furthermore, macrophages are thought to play a role in immune response by presenting foreign antigens (i.e., are antigen-presenting cells) to lymphocytes. The macrophages have been shown to be able to bind "nonself" pathogens directly, or they recognize pathogens as foreign because they have been coated by antibodies or complement. The exact recognition mechanism is unknown, but it has been proposed that receptors with broad binding specificity are used to discriminate between self and nonself.

Scavenger receptors are macrophage cell membrane proteins that can bind a variety of substances and facilitate their uptake and removal from blood or connective tissue (see Krieger and Hertz, *Ann. Rev. Biochem.* 63, 601–637, 1994). The macrophage scavenger receptors have been suggested to play a role in the binding of foreign antigens, in addition to their apparently important role in atherogenesis. These receptors have unusually broad ligand binding specificity and, thus, differ from many other cell surface receptors.

Scavenger receptors of types I and II are trimeric membrane proteins with a small N-terminal intracellular domain, a transmembrane domain, and an extracellular portion containing a short spacer domain, an α-helical coiled coil domain, and a short triple-helical collagenous domain (Krieger and Hertz, *Ann. Rev. Biochem.*, 63,601–637, 1994).

The type I scavenger receptor differs from the type II scavenger receptor in that it contains an additional C-terminal cysteine-rich domain. These receptors, which are present in macrophages in diverse tissues, such as liver and lung, have been shown to bind a variety of ligands such as chemically modified lipoproteins and albumin, polyribonucleotides, polysaccharides, phospholipids, asbestos etc. It has been proposed that the scavenger receptors play a key role in the development of atherosclerosis where they mediate macrophage uptake of modified low density lipoproteins (LDL) in arterial walls. Furthermore, the scavenger receptors are likely to function in host defense as some forms of gram-negative bacterial endotoxin and gram-positive bacteria can serve as their ligands. The collagenous domain of the scavenger receptor has been shown to mediate the binding activities assigned to these receptors.

The collagenous domain of the scavenger receptor is a triple helix formed by three chains which contain 24 consecutive Gly-Xaa-Yaa-triplets. Such Gly-Xaa-Yaa-triplets are the hallmark of the α chains of collagens, which are a family of extracellular proteins constituting the major structural proteins of the extracellular matrix. There are several proteins without structural functions that contain collagenous domains. As the scavenger receptors, most of those belong to the host defense mechanisms, such as complement factor C1q, conglutinin, mannose binding proteins, and pulmonary surfactant associated proteins. All these proteins are thought to participate in the removal of extracellular debris such as pathogenic material. Furthermore, enzymes such as acetyl cholinesterase and bacterial pullulanase contain collagenous domains.

Along these lines, applicants have identified and characterized a novel and unique macrophage receptor with collagenous structure. This protein, which shows structural homology with scavenger receptor type I, was expressed strongly after birth in a subset of macrophages in mouse spleen and lymph nodes. Furthermore, it is expressed in peritoneal macrophages, but not by macrophages of the liver or lung. The receptor was shown to bind bacteria and acetylated LDL, but not yeast. Based on its binding activity and distribution, the biological role of this receptor is believed to be related with immune defense and/or phagocytosis. The results suggest that the novel protein discovered by applicants is a macrophage-specific membrane receptor which has a role in host defense as it is expressed after birth in subpopulation of macrophages that are considered responsible for the binding of bacterial antigens and phagocytosis.

SUMMARY OF THE INVENTION

The present invention is directed to processes for isolating and identifying the nucleotide sequence of a gene for a novel macrophage receptor with collagenous structure, termed "MARCO" by the applicants. The new macrophage receptor with a collagenous domain binds gram positive and negative bacteria and acetylated LDL. Moreover, the invention relates to the nucleotide sequence for MARCO identified by the process of the invention and the isolated and purified polypeptide chain encoded by such a nucleotide sequence.

Further, the invention provides for the use of the identified nucleotide sequence, or DNA fragments thereof, to prepare DNA or RNA probes, radiolabeled, enzyme-labeled, chemiluminescence-labeled, avidin or biotin-labeled, or containing modified nucleotides, incorporated into a self-replicating vector, a viral vector, linear or circular, to detect the presence of the gene or mutations in the gene which can directly or indirectly produce disease. The invention also relates to the use of gene fragments from human genomic or cloned DNA for detection and analysis of the gene.

Additionally, the invention provides for the use of identified DNA sequence to correct for gene defects leading to mutations causing a malfunctioning MARCO. The instant invention also provides for methods for detecting the presence of specific MARCO mRNA in cells and tissues with an effective amount of nucleic acid probe, which probe contains a sense or antisense of MARCO mRNA sequence. In particular, the probes containing the identified nucleotide sequence or fragments thereof, radiolabeled, enzyme-labeled, chemiluminescence-labeled, avidin or biotin-labeled, or containing modified nucleotides, incorporated into a self-replicating vector, a viral vector which can be linear or circular.

The instant invention also provides for methods for generating the MARCO protein as recombinant protein or fragments thereof by inserting the gene into micro-organisms and expressing it in micro-organisms or eukaryotic cells. Similarly, the invention provides for the synthesis of peptides from the MARCO polypeptide chain based on the amino acid sequence derived from the coding sequence of the cloned gene.

The present invention also provides for the generation of immunoreactive antibodies, made against the MARCO protein or parts thereof, including synthetic peptides, that specifically detect the receptor protein and which can be used to detect the expression of the receptor in tissue, cell and fluid samples as well as for interfering with the binding of ligands such as bacteria to the macrophage receptor.

Furthermore, the present invention involves several different embodiments. The invention provides clones coding for the entire mouse MARCO polypeptide chain. The invention is directed, in particular, to a full-length mouse cDNA clone Maf-6. In addition, the invention provides for nucleotide sequences which encode the entire mouse amino acid sequences of the MARCO polypeptide. Furthermore, the invention provides for vectors containing parts of the mouse Maf-6 cDNA for the production of recombinant proteins. The invention also provides for two types of polyclonal antibodies recognizing the intra and extracellular domains of murine MARCO, respectively.

These and other objects and features of the invention will be apparent from the following drawings, detailed description of the invention and from the claims. It should, however, be understood that the detailed description and the specific examples, while indicating preferred embodiments of the invention, are given by way of illustration only, since various modifications and changes within the spirit and scope of the invention will become apparent to those skilled in the art.

BRIEF DESCRIPTION OF THE DRAWINGS

The file of this patent contains at least one (1) color photograph. Copies of this patent with color photograph(s) will be provided by the U.S. Patent Office upon request and payment of the necessary fee.

The following is a brief description of the drawings which are presented for the purpose of illustrating the invention and not for the purpose of limiting same.

FIGS. 2A and B show the nucleotide sequence (first line) of the murine MARCO chain cDNA (SEQ ID NO: 1) and its predicted (deduced) amino acid sequence (second line) shown with the one letter code (SEQ ID NO: 2). The tentative transmembrane domain II is indicated by an underline and cysteine residues and the two potential glycosylation sites are circled. The 3' end termination codon is indicated by "ter". A putative polyadenylation signal AATAAA is double-underlined.

In FIG. 5A, intense gold label can be seen on the cell surface proper and pseudopodia (×10,000). FIG. 5B is magnification (×50,000) of pseudopodia. No label was observed with antibodies against domain I (not shown).

In FIG. 7A, protein from spleen and kidney was extracted, immunoprecipitated with antisera against recombinant domains I (N) or V (C) of MARCO, electrophoresed on a 5% gel without reduction and immunoblotted. The antisera precipitated a 210,000 dalton protein from spleen (lanes 1 and 2), while no proteins were precipitated from the kidney (lanes 3 and 4) extract. The broad band of about 160,000 daltons seen in both spleen and kidney samples is immunoglobulin. When the same samples were electrophoresed on 8% gels after reduction, a major band of about 80,000 daltons was present in the spleen sample (lane 5), but not in that of kidney (lane 6). A broad ~50,000 dalton band representing IgG chains was seen in both samples. In FIG. 7B, protein extracts of $^{35}$S-methionine-labeled COS cells transfected with the MARCO cDNA (MARCO) or the same cDNA in the opposite orientation (control) were immunoprecipitated with MARCO antiserum, electrophoresed and processed for autoradiography. After a 4-hour pulse the immunoprecipitate migrated as a 210,000 dalton protein doublet under nonreducing conditions on 5% SDS-PAGE (lane 1). After reduction the major band had a size of about 60,000 daltons, with additional bands corresponding to differentially glycosylated forms of up to 80,000 daltons were also present (lane 3). After 18 hrs chase two bands of 70,000 daltons and a doublet of about 80,000 daltons remained (lane 4). Incubation with Tunicamycin revealed a band of 50,000 daltons (lane 5). No specific protein was precipitated from control samples (lanes 2 and 6).

DETAILED DESCRIPTION OF THE INVENTION

The applicants have discovered a novel gene encoding for a previously unknown protein. The DNA-derived amino acid sequence of the protein is unique, not existing in the available data bases. The protein is a novel murine plasma associated protein expressed postnatally by subpopulations of macrophages. The new polypeptide chain (SEQ ID NO: 2), which was shown to be a one of three, presumably identical subunit chains of a macrophage membrane receptor with a collagenous structure, has been designated as "MARCO" for macrophage receptor-collagenous.

The MARCO polypeptide chain was discovered by the isolation and nucleotide sequencing of cDNA clones which were identified during the screening of a mouse macrophage cDNA library with a human type XIII collagen DNA probe. This screening yielded several overlapping clones coding for a previously undescribed collagenous sequence, and rescreening of the same library with one of the cDNA inserts yielded new clones one of which, Maf-6 (FIG. 1), spanned a 1.8 kb sequence.

Figure 1:
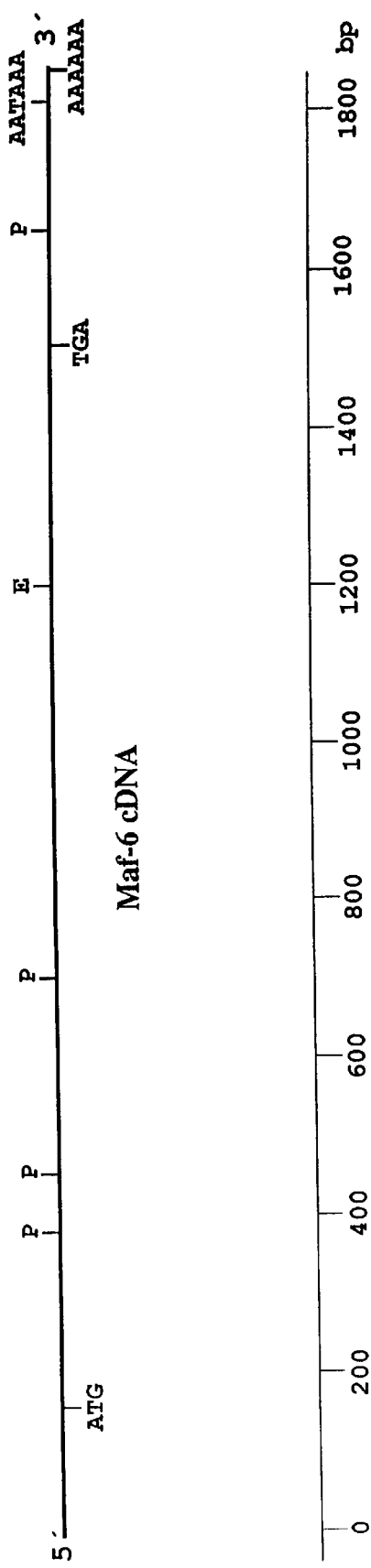
FIG. 1 shows restriction map of a cDNA clone (Maf-6) coding for the mouse MARCO subunit polypeptide chain. The 5'- and 3'-end orientations are indicated. Restriction endonuclease cleavage sites EcoRI (E) and Pst I (P) are shown. The translation initation site (ATG) and termination (TGA) sites and a potential polyadnylation site (AATAAA) are shown as well as a poly (A) tail (AAAAAA). Scale in base pairs is shown below the clone.
Figure 2A:
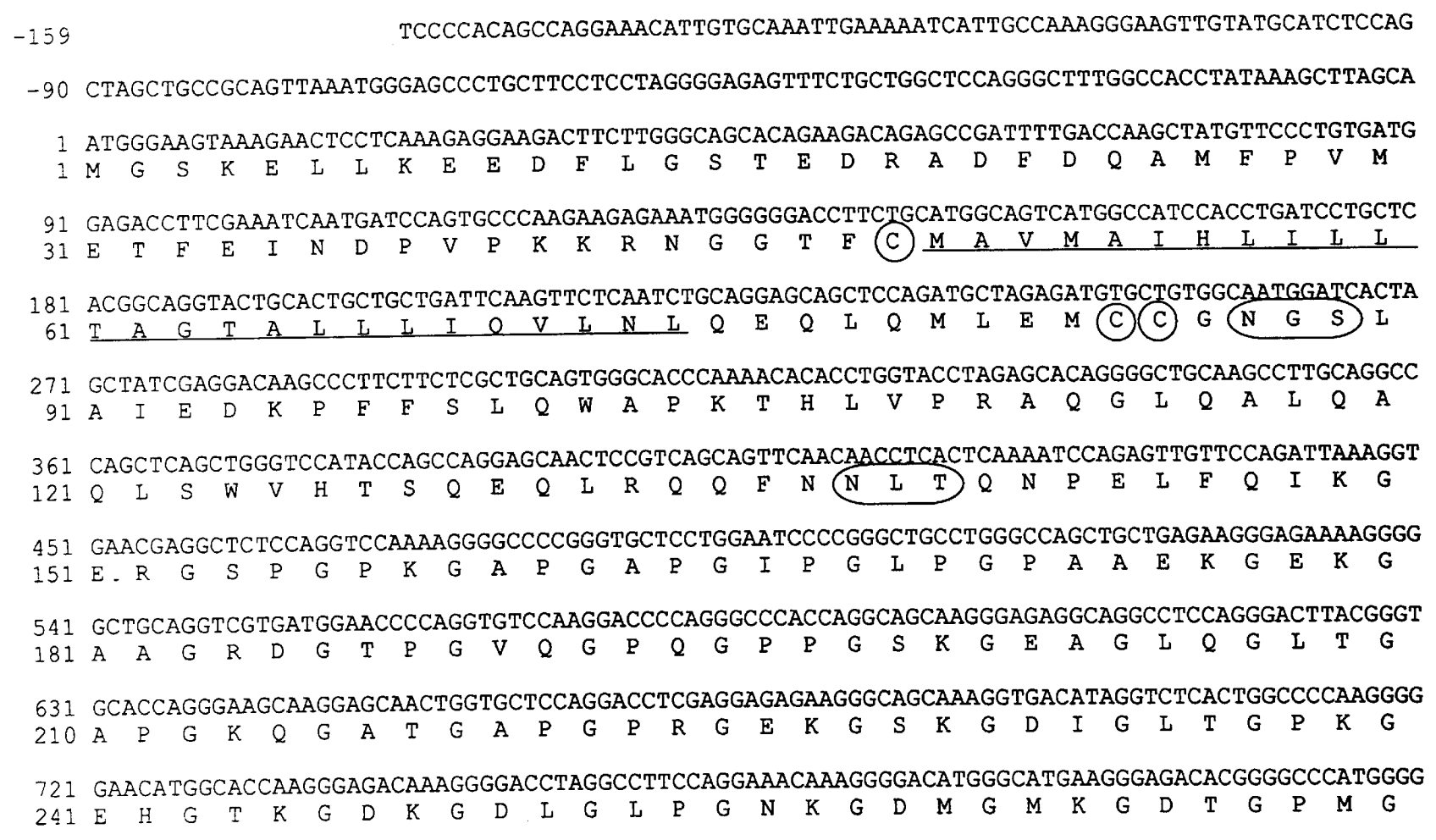

The sequence of Maf-6 (SEQ ID NO: 1) contained a 159 bp 5'-end untranslated region, a 1554 bp open reading frame, followed by an over 156 bp 3'-end untranslated region containing a TGA translation stop codon, a putative AATAAA polyadenylation signal and a poly(A) tail (FIGS. 1 and 2). The sequence surrounding the putative initiator methionine codon ATG does not agree completely with the Kozak consensus sequence, but it can be designated as strong translation initiation site when considering positions −3 and +4 (Kozak, M., The scanning model for translation: An update, *J. Cell. Biol.* 108, 229–241 (1989)).

Analysis of the 1554 bp open reading frame predicted the sequence for a unique 518 residue polypeptide not existing in the data base (FIG. 2). The molecular weight of this polypeptide chain was calculated to be 52,738.

Figure 3:
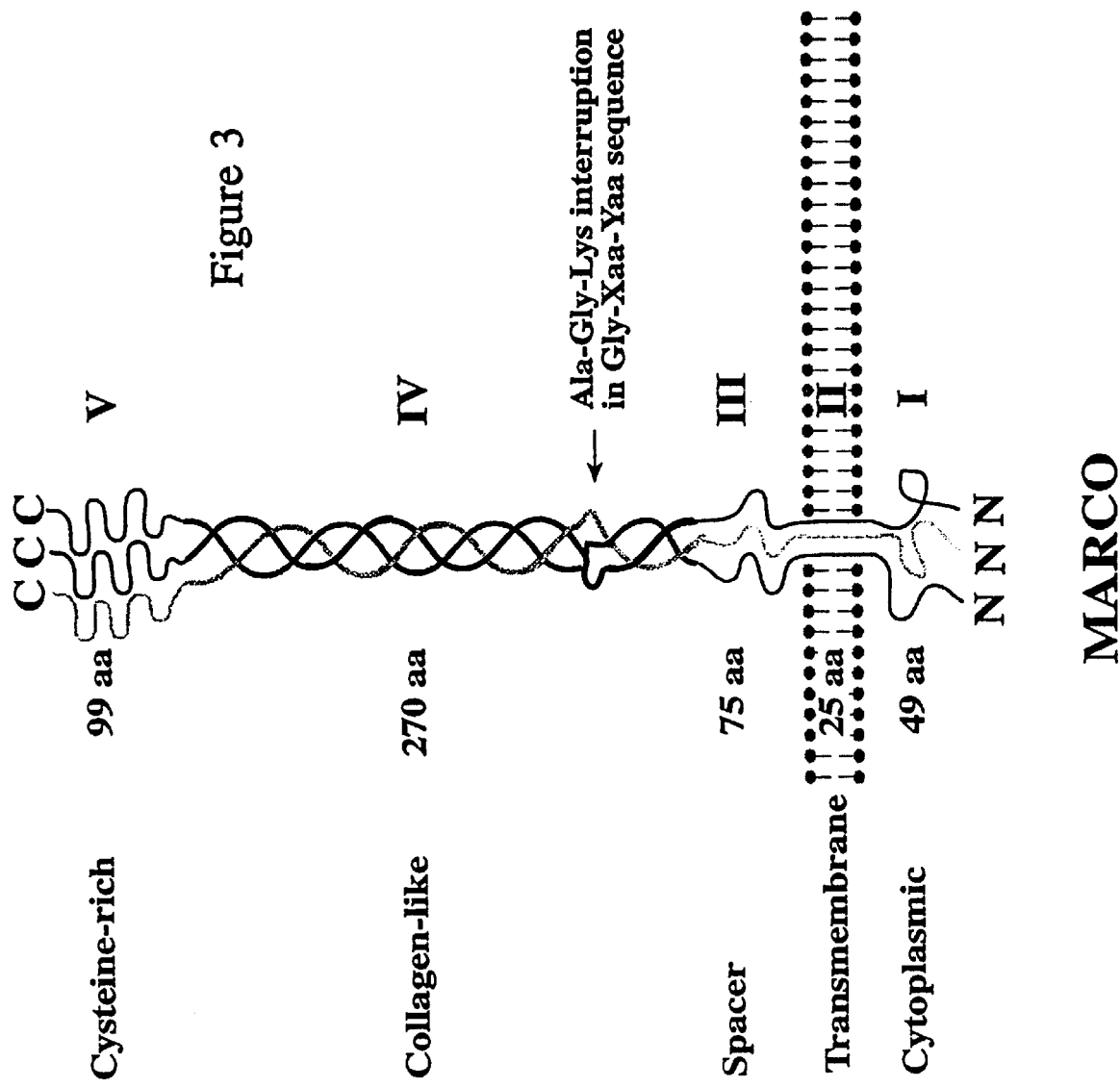
FIG. 3 depicts the predicted tertiary structure of the macrophage MARCO receptor. The MARCO receptor is a trimeric protein containing an N-terminal end intracellular domain I, a transmembrane domain II, and an extracellular domain consisting of a "spacer" domain III, a collagenous domain IV with 89 Gly-Xaa-Yaa-repeat sequences interrupted at one location and a C-terminal end cysteine-rich domain V.

The amino acid sequence indicated the presence of several distinct domains. The open reading frame starts with an ~50-residue rather hydrophilic domain I which starts with the initiator methionine and contains one cysteine. See FIGS. 2 and 3. Therefore, this protein does not contain a hydrophobic signal peptide-like sequence characteristic for secreted proteins. Domain II has an ~25-residue hydrophobic sequence, which is followed by a hydrophilic domain III containing 75 residues, including two cysteine residues. Domain III also has two putative N-glycosylation sites (FIG. 2). The sequences of domains I, II and III are each unique.

Domain IV has a 270-residue collagenous sequence characterized by 89 Gly-Xaa-Yaa triplets interrupted at one location (residues 174–176) by the sequence Ala-Glu-Lys. The C-terminal globular domain V which has 99 residues, six of which are cysteine. The sequence of this domain showed 48.9% sequence identity with the C-terminal domain of scavenger receptor type I (Krieger and Hertz, 1994). With the exception of the collagenous domain IV, the other domains did not show significant homology with scavenger receptors or other known proteins. As indicated above, the novel collagenous macrophage receptor with collagenous structure described here is referred to by the applicants as MARCO.

Since the initial cDNA clones for MARCO were isolated from a macrophage cDNA library, the applicants examined if the protein is expressed in some other cells or tissues. In order to obtain an overall picture of the spatial expression of MARCO, Northern analyses were first carried out on RNA isolated from several mouse tissues, freshly isolated peritoneal macrophages and cultured cells. Using mRNA from adult mice, strong signals were observed with RNA from spleen and peritoneal macrophages, but not in other tissues, including liver (data not shown).

Figures 4A, 4B, 4C, 4D:
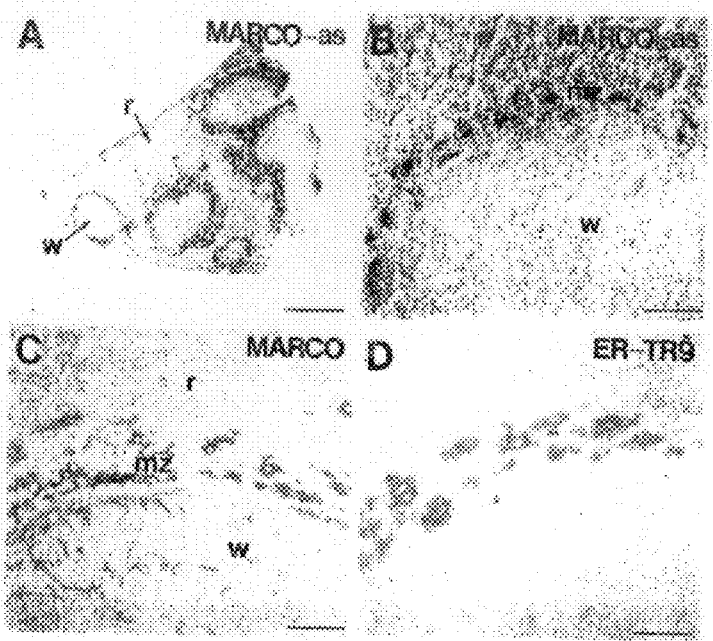
FIGS. 4A–4H show the results of in situ hybridization analyses of MARCO expression and comparison of immunolocalization of MARCO and macrophage R-TR9 and MOMA-1 antigens in mouse spleen and lymph node. Hybridization with the MARCO antisense probe (A,B) showed strong signals in cells located in a circle-like array in the marginal zone (mz) between the white (w) and red (r) pulps. Immunostaining with an antibody against the intracellular domain I of MARCO (C) and with the ER-TR9 antibody specific for marginal zone macrophages (D) showed codistribution of antigens. Double-staining with MARCO (blue) and MOMA-1 (red) antibodies showed some marginal zone macrophages positive for MARCO, but negative for ER-TR9 (E). Double-staining with MARCO (blue) and MOMA-1 (red) antibodies shows respectively, staining of marginal zone macrophages and metallophilic macrophages lining the marginal sinus (F). Hybridization with the MARCO antisense probe (G and H, dark and light fields, respectively) showed strong signals in cells located in the meduallary cord region of lymph node. E, capsule; mc, medullary cord; pc, paracortex. Bars in A, 800 µm; in C, D, E and F, 35 µm; in G and H, 400 µm.
Figure 4E:
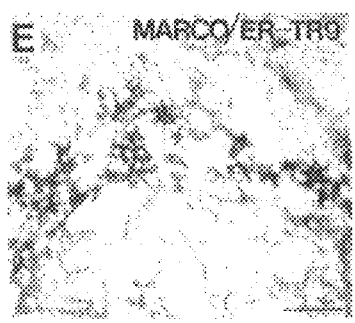
Figure 4F:
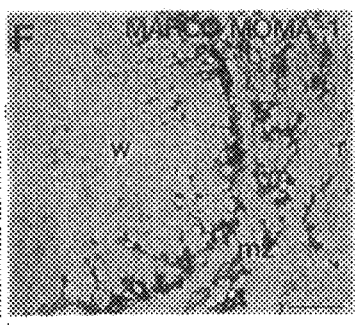
Figure 4G:
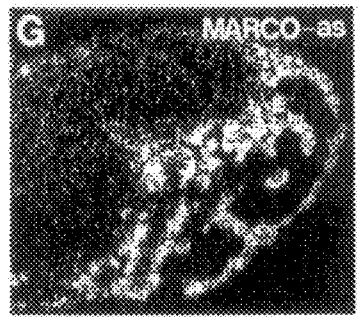
Figure 4H:
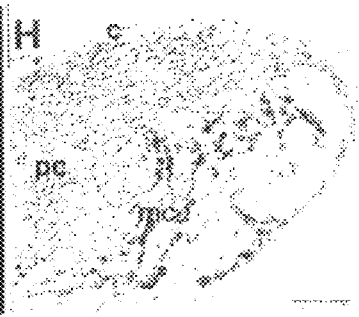

In order to more exactly determine the sites of MARCO expression, in situ hybridization was carried out on whole different age embryos and tissues from newly born and adult mice. The results showed no signals above background in the embryonic tissues (data not shown), but strong signals were seen with a MARCO antisense probe in a highly region-specific manner, both in spleen and lymph nodes (FIG. 4). Signals above background were not seen with the same probe in other tissues such as lung and liver, which are normally rich in macrophages (data not shown). The signals observed in the spleen were localized to macrophage-like cells in the marginal zone at the interface of the white and red pulps (FIGS. 4A, B). In lymph nodes strong signals were seen in cells of the medullary region which is rich in macrophages (FIGS. 4G, H). Similar anlyses with a sense probe did not reveal positive signals in any of the tissues studied (not shown).

The applicants also examined if MARCO is expressed in established macrophage cell lines using Northern analysis with mRNA isolated from a cultured macrophage cell line IC-21 (ATCC TIB 186), and the results revealed intense expression of an about 1.8 kb transcript (not shown).

In order to determine where the MARCO protein is located in vivo, antibodies were raised for immunohistological analyses. The putative extracellular globular domains IV and V and intracellular domain I of the MARCO polypeptide chain were expressed as glutathione S-transferase (GST) fusion proteins in the pGEX-1λT vector in E. coli, as described in Examples below, and then purified and used as antigens to raise antisera in rabbits. Immunostaining of frozen 2-month-old mouse spleen tissues revealed specific staining in macrophages located in the same region of the marginal zone (FIG. 4C) where expression was observed by in situ hybridization (FIGS. 4A, B). This indicates that MARCO is directly associated with the cells and not deposited into the extracellular matrix. Both antibodies gave identical results. No positive staining was observed in liver which is rich in scavenger receptor containing macrophages, indicating that the antibodies do not cross-react with the scavenger receptors.

Based on the immunohistochemical data, a close relationship was observed in the spleen between the expression of MARCO and the marginal zone macrophage marker ER-TR9 (Dijkstra, C. D., Van Vliet, E., Döpp, E. A., van der Lelij, A. A., and Kraal, G., Marginal zone macrophages identified by a monoclonal antibody: characterization of immuno- and enzyme-histochemical properties and functional capasities, *Immunology* 55, 23–28 (1985)). In the splenic marginal zone practically complete overlap was seen between the two macrophage markers (FIGS. 4C, D, E), and a similar correlation could be found for the expression of the two molecules in medullary macrophages in lymph nodes (not shown). Immunohistological staining of lymph node tissue with both MARCO antibodies stained macrophages located in medullary cords (not shown) in accordance with the expression pattern obtained with the in situ hybridization riboprobe (not shown). This correlates completely with the expression of ER-TR9 as previously reported (Dijkstra et al., 1985).

Figures 5A, 5B:
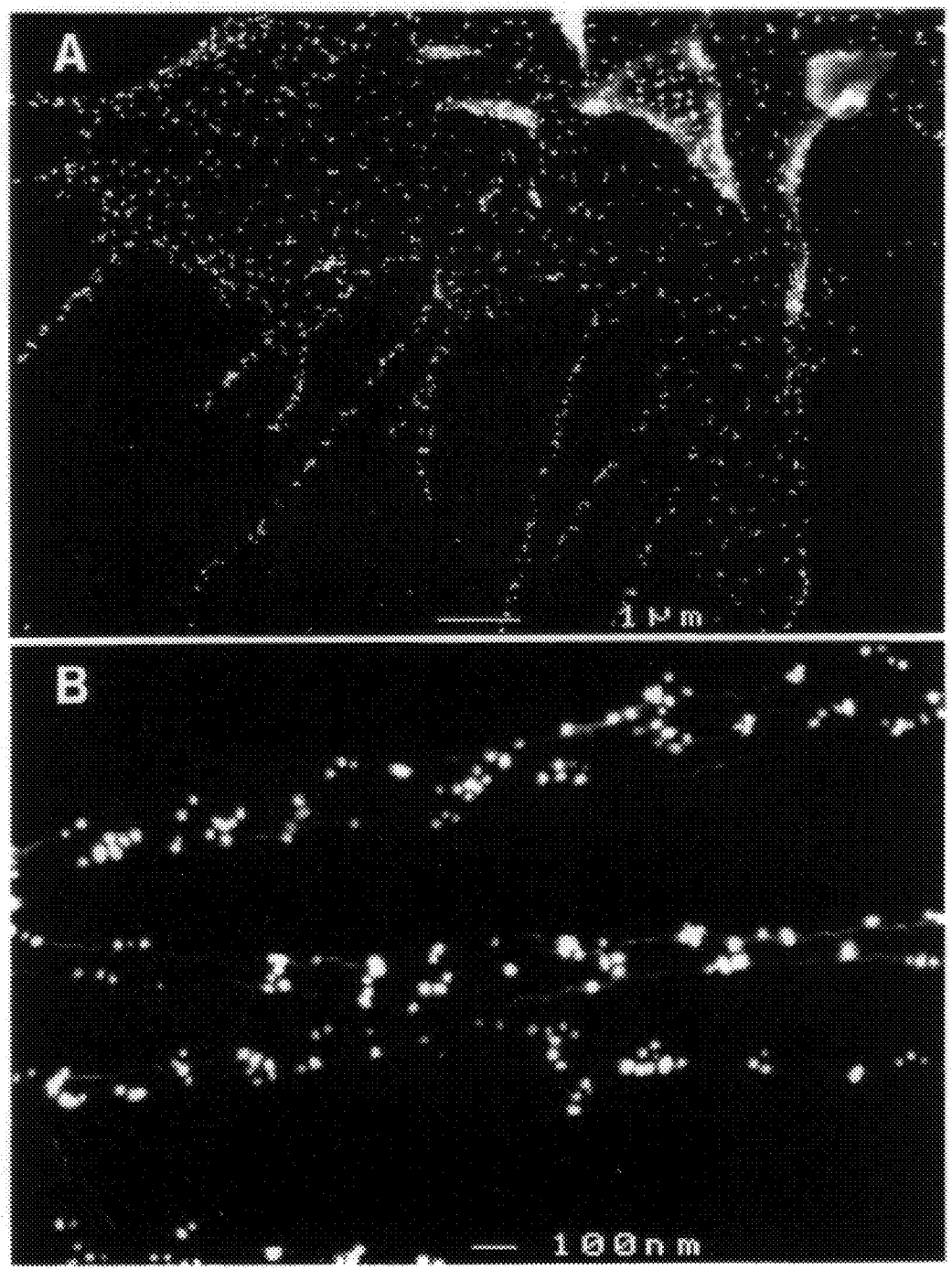
FIGS. 5A–5B shows localization of the MARCO protein on the surface of cultured IC-21 macrophages using field emission scanning immunoelectron microscopy carried out with a polyclonal antibody against the extracellular domain.

The following experiments (for more specificity, see the Examples below) were carried out by the applicants to determine the orientation of MARCO on the macrophage plasma membrane. First, cultured transformed IC-21 macrophages shown to normally express MARCO were processed for field emission scanning electron microscopy (FESEM) of the cell surface and reacted with the antisera against the putative extracellular C-terminal or intracellular N-terminal domains made by the applicants, followed by incubation with a gold-labeled second antibody. The antibody against the C-terminal domain V readily bound to the cell surface (FIGS. 5A and 5B), while the antibody against the N-terminal domain I did not (data not shown). The antibodies decorated the cell surface quite evenly and they also bound strongly to pseuodopodia which could protrude quite long distances from the cell membrane. In a second set of experiments transmission immunoelectron microscopy was carried out with the antibodies and this revealed that MARCO is associated with the plasma membranes. Together, these results demonstrated that MARCO is a membrane protein, and that within the plasma membrane domain I is located intracellularly and domain V extracellularly.

Figure 6:
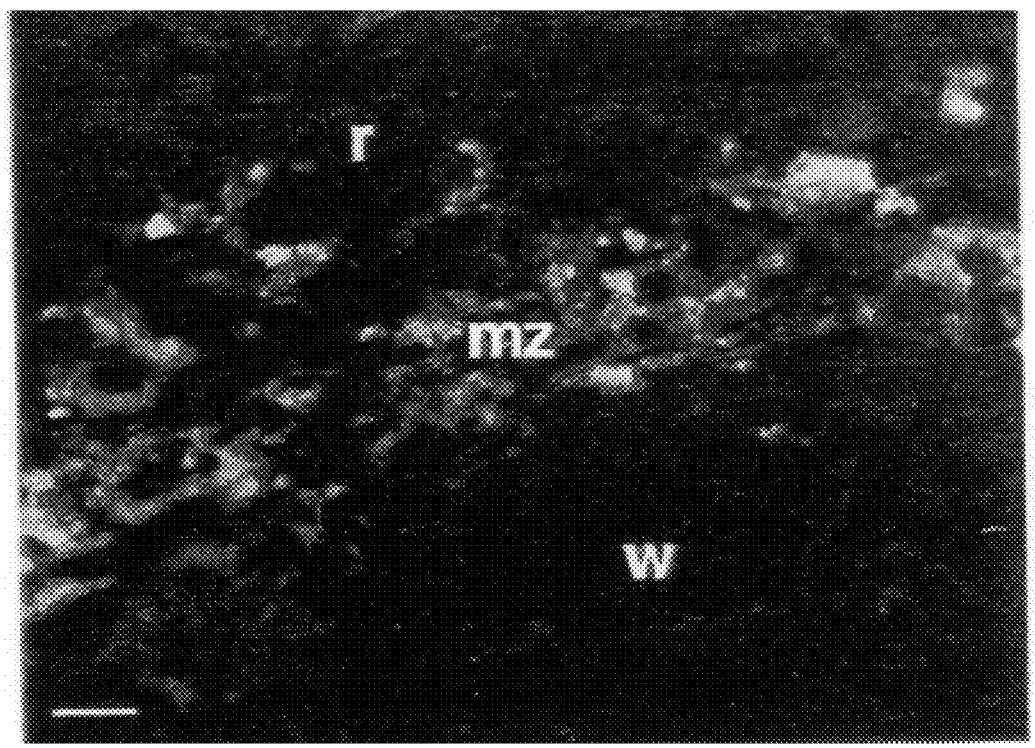
FIG. 6 demonstrates binding of MARCO antibodies to spleen marginal zone macrophages in vivo. Rabbit antiserum to the extracellular domain V of MARCO was injected intravenously into mouse after which tissue was removed and processed for staining using a FITC-labeled anti-rabbit IgG. The label was confined to marginal zone (mz) macrophages located between the red (r) and white (w) pulps. Antibodies against domain I did not bind cells (not shown).

In a third experiment carried out to examine the orientation of MARCO in the plasma membrane, antisera against domains I or IV and V were injected intravenously into mice, after which the tissues were processed, cryosectioned and analyzed for staining using an FITC-conjugated second antibody. In the spleen the strong staining was observed in marginal zone macrophages when the antiserum against domain V was used (FIG. 6), whereas no staining was observed in spleen sections of mice injected with the antiserum against domain I (data not shown). Also, other tissues such as liver were negative in this experiment, indicating that the protein is mainly present in spleen. These results support the hypothesis that the N-terminal domain I, and C-terminal domains IV and V are intracellular and extracellular, respectively.

Figure 7B:
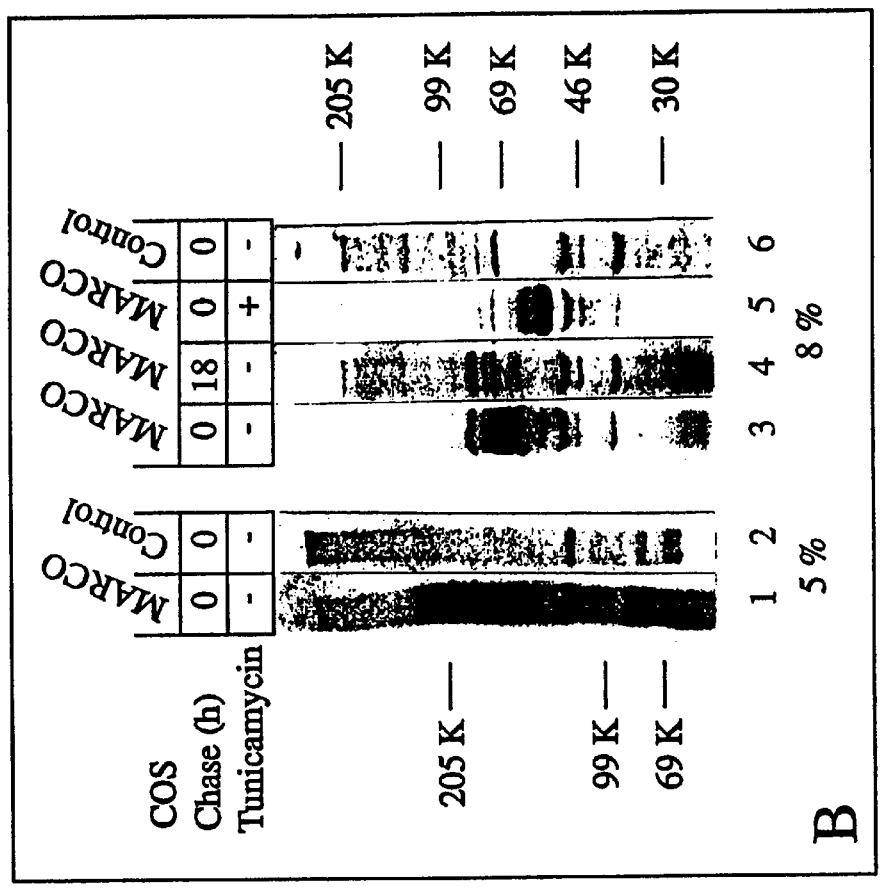
FIGS. 7A–7B show immunoprecipitation and immunoblot analyses of MARCO protein from mouse tissues and transfected COS cells.
Figure 7A:
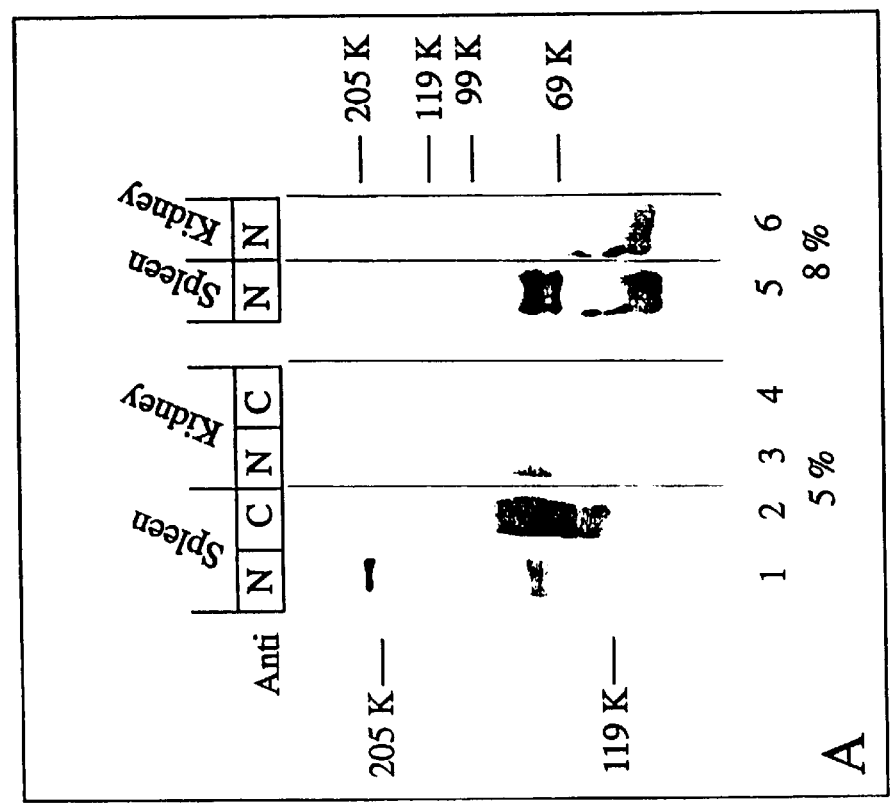

It could be hypothesized that MARCO is a trimeric protein with a triple-helical domain similar to those in collagenous proteins, based on the fact that the MARCO subunit chain contained a 270-residue long Gly-Xaa-Yaa-repeat containing sequence. Furthermore, the presence of several cysteines in the polypeptide suggested that the chains might be disulfide-linked in such a trimer. In order to examine this, the applicants extracted protein from intact mouse spleen and kidney (negative control) tissues, and carried out immunoprecipitation with the antibodies against domains I or V of MARCO, followed by immunoblotting as more particularly described in the Examples below. This study revealed that when the spleen extract was immunoprecipitated, electrophoresed on a 5% gel without reduction and immunoblotted, a major band of about 210,000 daltons and a second slightly smaller, weaker band, were seen with both antibodies (FIG. 7A lanes 1 and 2). A broad band of about 160,000 daltons representing IgG was also present. These bands disappeared when the samples were electrophoresed after reduction, while one diffuse major band of about 80,000 daltons and one weaker, slightly smaller band appeared (FIG. 7A lane 5). In addition, a strong 50,000 dalton band representing IgG was present. No specific protein was precipitated from the kidney extract with the MARCO antibodies (FIG. 7A, lanes 3, 4 and 6). These results strongly suggest that the MARCO molecule has a trimeric conformation containing interchain disulfide bonds. The nature of the weaker, smaller bands is not sure, but since they were recognized by both antibodies, they might represent forms with different post-translational modifications.

The applicants carried out further characterization of the MARCO protein using by metabolic labeling of transfected COS cells. COS cells, which normally do not express MARCO, were transfected with full-length cDNA to study glycosylation of the chains and also if native MARCO trimers can be formed with a single type of chains. Furthermore, labeling studies were carried out in the presence of Tunicamycin in order to examine if the minor heterogeneity of specifically immunoprecipitated bands might be due to differences in degree of glycosylation. Incubation with Tunicamycin, which inhibits N-glycosylation, revealed a MARCO chain with a size of ~50,000 daltons which agrees well with the calculated size based on the amino acid sequence predicted from the cDNA (FIG. 7B, lane 5). In pulse-chase experiments, cells were first pulsed for 1 or 4 hours and the label was then chased for up to 18 hours. After the pulse the major band had a size of about 60,000 daltons, but additional specifically immunoprecipitated bands had sizes of up to 80,000 daltons after reduction (FIG. 7B, lane 3). After 18 hours chase the 60,000 dalton bands had disappeared, but two bands of 70,000 daltons and a doublet of about 80,000 remained (FIG. 7B, lane 4). These results suggest that the microheterogeneity of sizes of the subunit chains of MARCO is due to differences in glycosylation, but not proteolysis as these proteins were detected with antibodies reacting with both ends of the polypeptide (data not shown).

Figures 8A, 8B, 8C, 8D, 8E, 8F:
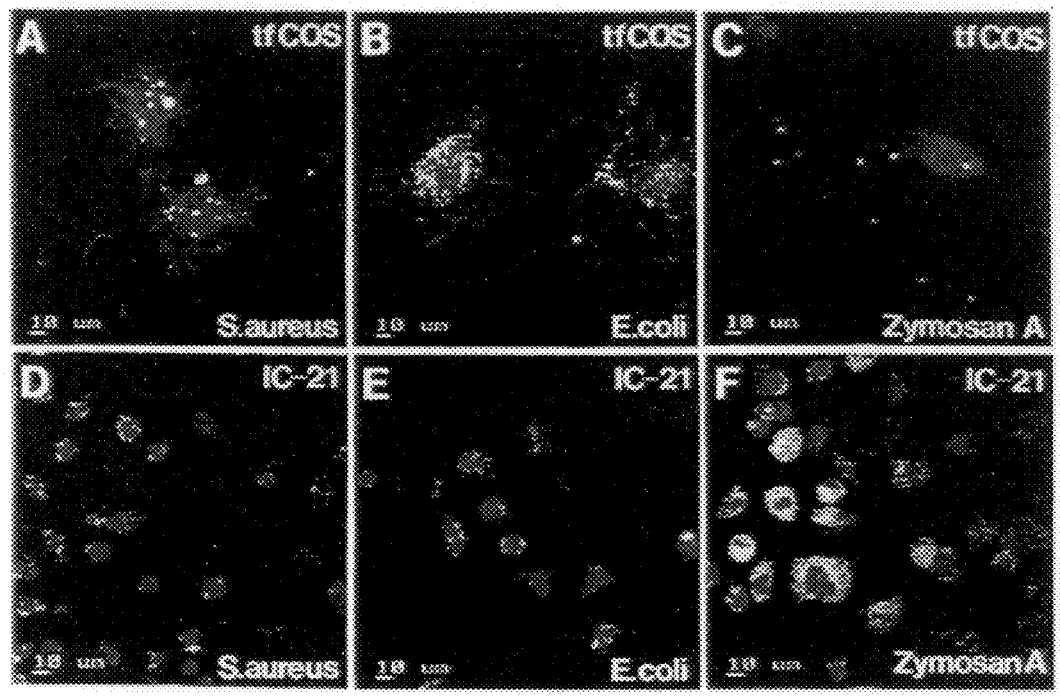
FIGS. 8A–8F illustrate binding of fluorescein-labeled *E. coli*, *S. aureus* and Zymosan A (*S. cerevisiae*) bacteria to MARCO receptors on cells transfected with full-length cDNA. Transfected COS cells or IC-21 macrophages were incubated with FITC-labeled *S. aureus* (A, D), *E. coli* (B, E) and Zymosan A (C, F) and the MARCO expressing COS cells were visualized by immunostaining with MARCO antibodies and a rhodamine labeled secondary antibody. The IC-21 cells were stained with ethidium bromide. MARCO positive COS cells, but not negative control COS cells showed specific binding of *E. coli* and and *S. aureus* (A, B), while these cells did not bind Zymosan A (*S. cerevisiae*) (C). In contract, the IC-21 macrophages bond all three probes (D,E,F). This binding was shown to be specific as it could be inhibited by incubation of the cells prior to the addition of the labeled bacteria (E).

Pulse-labeled immunoprecipitated MARCO extracted from the transfected cells was electrophoresed on SDS-PAGE without reduction and compared with MARCO immunoprecipitated from a spleen tissue extract. The results showed that the sizes of trimeric MARCO proteins from the COS cells (FIG. 7B, lane 1) and spleen (FIG. 7A, lanes 1 and 2) corresponded to each other. COS cells transfected with a construct containing MARCO cDNA in the wrong orientation did not reveal specific bands after immunoprecipitation (FIG. 8B, lanes 2 and 6). Together, the labeling data demonstrated that the transfected cells were able to synthesize single MARCO chains and assemble them into disulfide-bonded homotrimers.

The applicants also studied if the homotrimers are transported to the plasma membrane using immunoelectron microscopy and this revealed staining for the MARCO chain mainly in plasma membranes of the transfected cells, indicating that the trimer was actually integrated into the plasma membrane (data not shown).

The marginal zone macrophages in the spleen have been proposed to play a key role in the host-defense system by recognizing and phagocytosing blood pathogens such as bacteria and yeast. For example, the cells can selectively take up neutral polysaccharides present on bacterial walls. To initially characterize the potential binding properties of MARCO, cultured transfected COS cells, and IC-21 macrophages used as positive control cells, were incubated with several fluorescein-labeled bioprobes. When transfected COS cells expressing MARCO were incubated with labeled E. coli and S. aureus bacteria, specific binding was seen to cells which were immunopositive with MARCO antibodies (FIGS. 8A, B). In contrast, labeled S. cerevisiae (Zymosan A) did not bind to COS cells expressing MARCO (FIG. 8C). Cultured IC-21 macrophages bound all three probes (FIGS. 8D–F). As negative control, COS cells transfected with a plasmid containing MARCO cDNA in the wrong orientation did not bind any of the probes (not shown).

Figure 9:
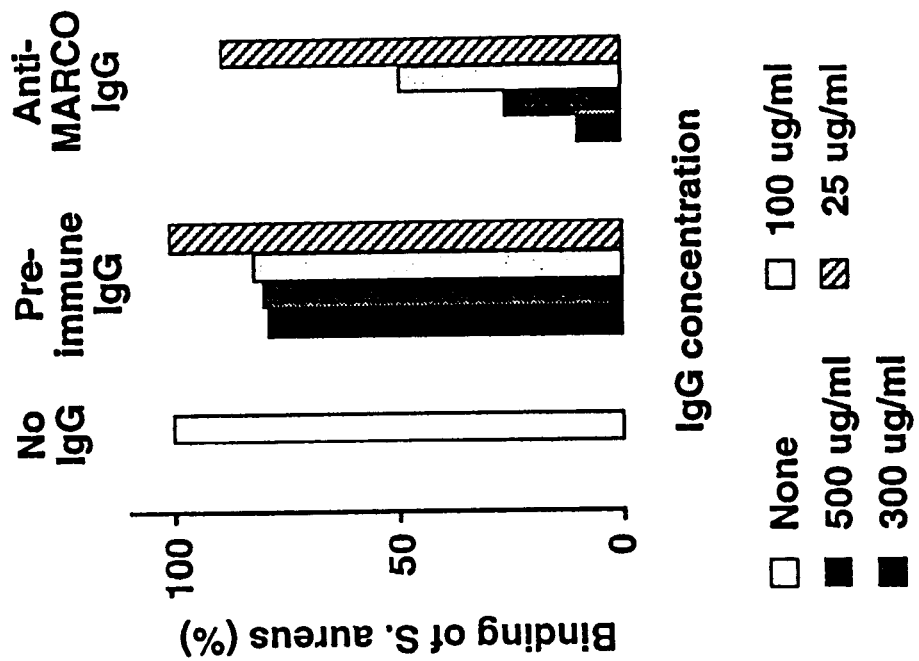
FIG. 9 illustrates how antibodies against the extracellular domains IV and V of MARCO inhibit the biding of FITC-labeled *Staphylococcus aureus* bacteria to COS cells transfected with full-length MARCO cDNA and expressing native MARCO receptor.

The binding of S. aureus could be inhibited efficienity by antiserum (not shown) and IgG (FIG. 9) raised against domains IV and V. Binding of E. coli could also be inhibited by these antibodies (not shown).

Figures 10A, 10B:
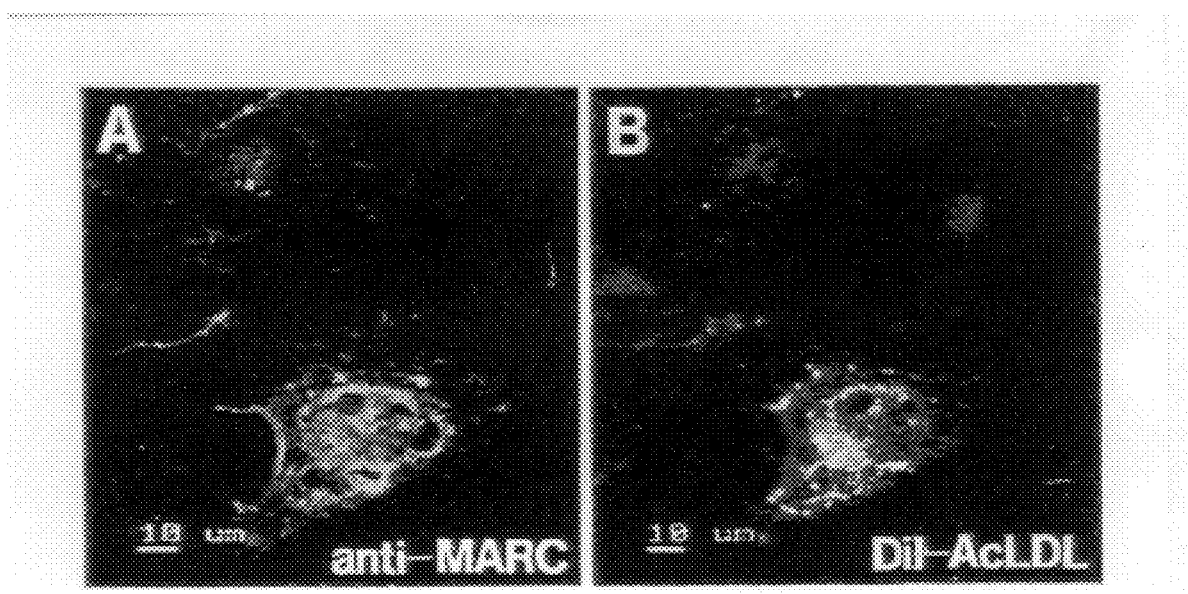
FIGS. 10A–10B show binding of DiI-labeled AcLDL to COS cells expressing the MARCO receptor. The MARCO expressing cell were incubated with DiI-AcLDL (5 μg/ml) and visualized with MARCO antiserum and a FITC-labeled secondary antibody. Immunopositive COS cells (A) readily bound DiI-AcLDL (B).

Due to the structural homology of MARCO with macrophage scavenger receptors which bind a variety of ligands such as acetylated LDL, the applicants also investigated if MARCO cDNA transfected COS cells bind this compound. The results showed that MARCO expressing COS cells readily bound DiI-acetylated LDL (FIG. 10).

Accordingly, applicants' study provides the first description of a unique plasma membrane-bound macrophage receptor with collagenous structure (MARCO) expressed in specific subpopulations of macrophages in spleen, lymph nodes as well as in peritoneum. This receptor was shown to bind both gram positive and negative bacteria and acetylated LDL, but not yeast. The structure of MARCO resembles to some extent that of scavenger receptor type I (Kodama, T. Freeman, M., Rohrer, L., Zabrecky, J., Matsudaira, P., and Krieger, M., Type I macrophage receptor contains α-helical and collagen-like coiled coils, Nature 343, 531–535 (1990)) which also is a macrophage specific protein. However, MARCO is clearly a distinct gene product with somewhat different binding properties than the scavenger receptor.

In addition, the following observations were also concluded from applicants' study:
A) MARCO (SEQ ID NO: 2) is a Membrane-Bound Trimeric Protein Based on the deduced amino acid sequence of the MARCO polypeptide which contains a 270-residue Gly-Xaa-Yaa-repeat sequence, it could be predicted that MARCO is a trimeric protein where this domain folds into a triple helix similar to that of collagens. This assumption gained support by experiments showing that MARCO extracted from both spleen tissue and transfected COS cells had a molecular weight of about 210,000 on SDS-PAGE without reduction. These experiments also demonstrated that the subunit chains are disulfide-bonded. The calculated molecular weight of a MARCO trimer containing unprocessed chains would be 160,000, but glycosylation of one or both of the two potential glycosylation sites in the MARCO polypeptides could explain a molecular weight of over 200,000 as determined by SDS-PAGE. The pulse-chase and Tunicamycin labeling studies carried out in this study.supported this assumption. As the collagenous sequence of the MARCO chain is interrupted at one site by the sequence Ala-Glu-Lys close to the N-terminal end of the collagenous domain, the triple helix of domain IV in MARCO is likely to have a "kink" or "hinge" as has been shown to be the case in collagens with interrupted triple helices such as type IV collagen (Hudson, B. G., Reeders, S. T., and Tryggvason, K., Type IV collagen: Structure, gene organization and role in human diseases. Molecular basis of Goodpasture and Alport syndromes and diffuse leiomyomatosis, J. Biol. Chem. 15, 26033–26036, (1993)). At the present, it is not known if the MARCO molecules in vivo are homo- or heterotrimers, but applicants experiments demonstrated that homotrimers can be formed in transfected COS cells from the MARCO subunit chain cloned in this study.

The primary structure of MARCO is that it is not a secreted protein, as it does not contain a typical signal peptide sequence as in the case for the scavenger receptors. The hydrophobic sequence of domain II which resembles that of the single transmembrane domain of the scavenger receptor chains further indicated that MARCO is a membrane protein and this was confirmed in various immunological studies which clearly localized the protein to the plasma membrane, but also to intracellular membranes. The fact that grains were seen in association with intracellular membranes in immunoelectron microscopy may not necessarily mean that MARCO functions intracellularly, as it is possible that the intracellular membrane association is due to newly synthesized MARCO which is being transported out of the cell or, alternatively, internalized MARCO.
B. MARCO Shows Structural Similarities with Scavenger Receptor Type I The primary structure of the MARCO subunit chain characterized here has higher similarity with the scavenger receptor chains than with any of the chains of structural collagens or other proteins with collagenous domains, including C1q, conglutinin, mannose binding proteins, pulmonary surfactant associated proteins, acetyl cholinesterase and bacterial pullulanase (Reid, K. B. M., Lowe, D. M., and Porter, R. R., Isolation and characterization of C1q, subcomponent of the first component of complement from human and rabbit sera, *Biochem. J.* 130, 749–763 (1972); Mays, C. and Rosenberry, T. L., Characterization of pepsin-resistant collagen-like tail subunit fragments of 18S and 14S acetylcholinesterase from *Electrophorus electricus*, *Biochemistry* 20, 2810–2817 (1981); Drickamer, K., Dordal, M. S., and Reynolds, L., Mannose-binding proteins isolated from rat liver contain carbohydrate-recognition domains linked N collagenous tails, *J. Biol. Chem.* 261, 6878–6887 (1986); Charalambous, B. M., Keen, J. N., and McPherson, M. J., Collagen-like sequences stabilize homotrimers of a bacterial hydrolase, *EMBO J.* 7, 2903–2909 (1988); Lee, Y.-M., Leiby, K. R., Allar, J., Paris, K., Lerch, B., and Okarma, T. B., Primary structure of bovine conglutinin, a member of the C-type animal lectin family, *J. Biol. Chem.* 266, 2715–2723 (1991); Krejci, E., Coussen, F., Duval, N., Chatel, J.-M., Legay, C., Puype, M., Vandekerckhove, J., Cartaud, J., Bon, S., and Massoulie, J., Primary structure of a collagenic tail peptide of Torpedo acetylcholinesterase: co-expression with catalytic subunit induces the production of collagen tailed forms in transfected cells, *EMBO J.* 10, 1285–1293 (1991); Petry, F., Reid, K., and Loos, M., Isolation sequence analysis and characterization of cDNA clones coding for the C chain of mouse, *Clg. Eur. J. Biochem.* 209, 129–134 (1992).

Furthermore, the predicted tertiary structure (FIG. 3) and the polarity of amino acids next to the hydrophobic domain II strongly indicate that MARCO is, indeed, an integral trimeric membrane molecule, where each chain has a single membrane-spanning domain and an N-terminal cytoplasmic domain I as in the scavenger receptor. The orientation of MARCO was verified by immunohistochemical and FESEM analyses which clearly demonstrated that domain V is extracellular and domain I intracellular.

In addition, it has been determined that the 75-residue extracellular domain III of the MARCO chain which corresponds to the 33-residue domain III in the scavenger receptor chains, probably participates in a "spacer" domain between the plasma membrane and the rod-like triple-helical domain IV of MARCO. The triple-helical domain IV of MARCO differs substantially from the coiled coil region formed by domains IV and V of the scavenger receptor. Domain IV of MARCO forms a triple-helical collagenous domain interrupted at one site by an Ala-Glu-Lys sequence, while the scavenger receptor has first a noncollagenous α-helical coiled coil followed by a classical collagenous triple helix which, however, is considerably shorter than that of MARCO. The C-terminal end domains V and VI of MARCO and scavenger receptor type I, respectively, are quite homologous, each containing six cysteine residues with similar spacing. This scavenger receptor cysteine-rich motif (SRCR domain) has been found in a number of other proteins. All of the known mammalian SRCR-domain-containing proteins are expressed on the surfaces of cells associated with the immune system and host defence functions (T cells, B cells and macrophages) or are secreted and known or suspected of being involved with host defence (Resnick, D., Pearson, A., and Krieger, M., The SRCR superfamily: a family reminiscent of the Ig superfamily, *Trends Biochem. Sci.* 19, 5–8 (1994)). As can be seen in FIG. 11, this sequence is highly conserved between MARCO and scavenger receptor, the sequence identity being 48.9% and sequence similarity 61.5% when conserved amino acid substitutions are taken into account.

C. Expression of MARCO in a Subset of Macrophages and Binding of Bacteria Indicates Role in Host Defense The expression of MARCO in specific macrophage subpopulations in lymphoid organs only is indicative of a role for MARCO in immunological reactions. It also emphasizes the heterogeneity within macrophage populations and the compartmentalization of the lymphoid system. The marginal zone macrophages of the spleen in which MARCO is highly expressed form, in many respects, a very special population. These large macrophages are strategically positioned in the anatomical compartment of the spleen where the bloodstream leaves the small arterioles into the "open" venous system (Kraal, G., Ter Hart H., Meelhuizen, C., Venneker, and Claassen, E., Marginal zone macrophages and their role in the immune response against T-independent type 2 antigens. Modulation of the cells with specific antibody, *Eur. J. Immunol.* 19, 675–681 (1989)). Here, in the marginal zone, the first contact of the phagocytosing system with blood borne pathogens takes place, and especially the highly phagocytic marginal zone macrophages can take up material, even without the need of prior opsonization.

Despite structural similarities with scavenger receptor type I, the MARCO molecule probably has different functions as it is present in different types of macrophages. For example, MARCO was not found in liver or lung tissues. However, as scavenger receptors, MARCO binds acetylated LDL and bacteria, but it differs by not binding yeast. The restricted expression of the MARCO receptor on macrophages capable of binding and possibly taking up acetylated LDL and located at sites in the spleen where they are in continuous contact with the blood stream points to a significant role in the clearance of serum components.

Taken together, the restricted expression of MARCO in subpopulations of macrophages which are involved in the uptake of (bacterial) antigenic polysaccharides, and the structural similarities with scavenger receptors indicate that MARCO plays an important role in the host defense system and homeostasis of the body.

The following examples further illustrate the specific embodiments of the present invention. It is to be understood that the present invention is not limited to the examples, and various changes and modifications may be made in the invention without departing from the spirit and scope thereof.

EXAMPLES

A. Experimental Procedures
Isolation and Characterization of cDNA Clones Coding for the Murine MARCO Polypeptide Chain A mouse macrophage cDNA library in λgt11 (Clontech ML1005) was screened with a human type XIII collagen DNA. Clones were screened to purity with $^{32}$P-labeled probes at low stringency conditions at +37° C. in 5×SSC, 5×Denhart's, 0.1% SDS, 50% formamide, 200 mg/ml salmon sperm DNA. Filters were washed with 0.2×SSC, 0.1% SDS at +42° C. Positive clones were isolated and subcloned into pUC18/19-or M1318/19-vectors with standard methods, and sequenced from both strands with the dideoxynucleotide chain-termination procedure using Sequenase enzyme (United States Biochemicals). Either universal primers or specific oligonucleotide primers were used in the sequencing.

RNA Isolations and Northern Analysis

Total RNA from tissues (liver, kidney, spleen, lung, brain and thymus) of about 2-month-old (adult) mice was extracted (Chomeczynski, P., and Sacchi, N., Single step method of RNA isolation by acid quanidium thiocyamate phenol chloroform extraction, *Anal. Biochem.* 162, 156–159, (1987)). mRNA was isolated directly from cultured cells or from total RNA with a slight modification of the Fast Track RNA isolation kit method (Invitrogen) by oligo dT cellulosa (Pharmacia). For Northern analysis mRNA was electrophoresed on a 1.0% agarose gel in the presence of formaldehyde. The RNA was transferred to nitrocellulose filters, which were hybridized with a MARCO cDNA insert labeled with $^{32}$P-dCTP by random priming. Prehybridization and overnight hybridization were done at +42° C. in 5×SSC, 5×Denhart's, 0.1% SDS, 50% formamide, 200 mg/ml salmon sperm DNA solution. Membranes were washed in 2×SSC, 0.1% SDS +42° C.

In situ Hybridization

In situ hybridization was carried out on whole 14 to 17 day-old mouse embryos and on lung, liver spleen, lymph nodes, kidney and heart tissues of 9-day-old pups, as well as on bone marrow, intestine, lung, liver, spleen, lymph nodes, kidney and thymus of adult mice. Tissues were dissected in phosphate-buffered saline, pH 7.3 and fixed in paraformaldehyde at +4° C. for 1 h or overnight, dehydrated, and embedded in paraffin wax. Sections of 7 μm were placed on silanized glass slides and stored at +4° C. until used. For the preparation of RNA probes, DNA fragments (nucleotides 65-398 and 2211-1672 in FIG. 2) were amplified by PCR using the Maf-6 cDNA clone as template. PCR primers contained restriction sites for subcloning into pSP64 and pSP65 plasmid vectors (Promega). The labeling of probes and in situ hybridization were performed (Wilkinson, D. G., and Green, J., In situ hybridization and the three dimensional reconstruction of serial sections. In Postimplantation mammalian embryos, A. J. Copp and D. L. Cockroft, eds. (Oxford: OUP), pp. 155–171 (1990)). Briefly, the plasmids were first linearized and [$^{35}$S]-UTP-labeled (1000 Ci/nmol, Amersham) probes were transcribed from the SP6 promoter. The probes were fractionated with Sephadex G-50 (Pharmacia), precipitated with ethanol, mixed with hybridization mixture, and placed on the pretreated sections. The sections were incubated overnight at +50° C., washed under high stringency condition, and dipped in autographic emulsion (Kodak NTB2) . After exposure for 11 days, the emulsion was developed and the sections were stained with hematoxylin and mounted.

Preparation of Antibodies

Monoclonal antibodies, ERTR-1 and MOMA-1, against macrophage antigens have previously been described (Dijkstra, C. D., Van Vliet, E., Döpp, E. A., Van der Lelij, A. A., and Kraal, G., Marginal zone macrophages identified by a monoclonal antibody: characterization of immuno- and enzyme-histochemical properties and functional capasities, *Immunology* 55, 23–28 (1985); Kraal, G., Ter Hart H., Meelhuizen, C., Venneker, and Claassen, E., Marginal zone macrophages and their role in the immune response against T-independent type 2 antigens. Modulation of the cells with specific antibody, *Eur. J. Immunol.* 19, 675–681 (1989)). For the production of polyclonal antibodies domains of the MARCO polypeptide were expressed as glutathione S-transferase (GST) fusion proteins in the pGEX-1λT vector (Pharmacia) in *E. coli*. DNA fragments encoding the putative extracellular domain IV and V (residues 369–518, FIG. 2) and intracellular domain I (residues 1–50, FIG. 2) of the MARCO polypeptide were generated by polymerase chain reaction (PCR) using primers containing restriction sites for cloning into the pGEX-1λT vector (Pharmacia). Sequences were confirmed by DNA-sequencing. Fusion proteins produced in bacteria were purified using glutathione Sepharose 4B (Pharmacia) and eluted with 5 mM glutathione. Purified MARCO polypeptides were mixed with Freund's adjuvant (Difco), and used for immunization of rabbits. Antisera were used after the third booster. IgGs were first purified by protein A Sepharose (Pharmacia) and then further purified by negative immunoabsorption from unspecific antibodies against the GST-protein and *E. coli* proteins using GST-*E. coli* total protein lysate coupled to CNBr-activated Sepharose 4B (Pharmacia).

Immunohistochemical Staining

Light microscopy immunohistochemical analyses were carried out on cryosections of mouse tissues. The sections were fixed in ethanol or acetone, air-dried and then used for immunostaining using either peroxidase or fluorescence dyes. For staining with monosclonal antibody against the macrophage marker ER-TR9 (Kraal, G., Ter Hart H., Meelhuizen, C., Venneker, and Claassen, E., Marginal zone macrophages and their role in the immune response against T-independent type 2 antigens. Modulation of the cells with specific antibody, *Eur. J. Immunol.* 19, 675–681 (1989)), sections were incubated with the antibody for 1 h at 4° C., washed twice with PBS and incubated with horse radish peroxidase (HRP)-conjugated rabbit anti-rat IgG second antibody (Dako, Denmark). After washing HRP activity was demonstrated with amino-ethyl carbazole (AEC) and $H_2O_2$ for 4 min., resulting in a red reaction product. For double staining the sections were thereafter incubated with rabbit anti-MARCO peptide antiserum against extracellular domain IV and V for 1 h at 4° C., washed and incubated with a swine anti-rabbit IgG-HRP conjugate (Dako, Denmark), HRP activity was now demonstrated using 4-chloro-1-naphtol and $H_2O_2$ for 4 min., resulting in a blue reaction product.

Immunolocalization

For staining with monoclonal antibody against the macrophage marker ER-TR9 (Kraal, 1992), crysections were first incubated with the antibody, and then with horseradish peroxidase (HRP)-conjugated rabbit anti-rat IgG second antibody (Dako, Denmark). HRP activity was demonstrated with amino-ethyl carbazole (AEC) and $H_2O_2$, resulting in a red reaction product. For double staining the sections were thereafter incubated with rabbit anti-MARCO IgG (100 μg/ml) against domains I or V and incubated with a swine anti-rabbit IgG-HRP conjugate (Dako, Denmark). HRP activity was now demonstrated using 4-chloro-1-naphtol and $H_2O_2$, resulting in a blue reaction product. For immunofluorescence microscopy sections were incubated with anti-MARCO IgG (100 μg/ml) and then with FITC-conjugated goat anti-rabbit IgG (Cappel).

For field emission electron microscopy cells were fixed with 4% and 8% paraformaldhyde for 10 min each, followed by incubation with anti-MACRO IgG anti-rabbit IgG labeled with 30 nm gold particles (Amersham). The cells were post-fixed with 2.5% glutaraldehyde, dehydrated in alcohol, dried in Balzers CPD 030 critical point dryer, coated with a thin carbon layer and examined in a Jeol JSM-6300 F electron microscope.

Immunoprecipitation

Immunoprecipitation was carried out with standard procedures (Sambrook, J., Fritsch, E. F., and Maniatis, T., Molecular Cloning: A laboratory Manual Second Edition. Cold Spring Harbor, N.Y., Cold Spring Harbor Laboratory Press (1989). Briefly, membranes were partially purified from mouse spleen and kidney (Schneider, W. J., Goldstein, J. L., and Brown, M. S., Partial purification and characterization of the low density lipoprotein receptor from bovine adrenal cortex, *J. Biol. Chem.* 255, 11442–11447 (1980)) and the membranes and cells were extracted into triple detergent buffer (50 mM Tris-HCl, pH 8, 150 mM NaCl, 1% Nonidet P-40, 0.1% SDS, 0.5% sodiumdeoxycholate, 100 mg/ml phenymethylsulfonyl fluoride (PMSF), 0.02% sodium azide, 1 mg/ml aprotinin). The extract supernates were then precleared by incubating with irrevelant serum followed by incubation with S. aureus cells (Fluka). The antigen was precipitated using polyclonal antisera or purified IgG against MARCO and incubated with protein A-Sepharose (Pharmacia). The protein A-sepharose-IgG complex was washed with NET buffer (50 mM Tris-HCl, pH 7.5, 150 mM NaCl, 0.1% Nonidet p-40, 1 mM EDTA, pH 8, 0.25% gelatin and 0.02% sodium azide) and then with 10 mM Tris-HCl, pH 7.5, 0.1% NP-40 solution, and heated in sample buffer at 95° C. in the presence or absence of 5% mercaptoethanol prior SDS-PAGE.

SDS-PAGE and Western Analysis

Reduced and nonreduced samples were separated by electrophoresis on 8% or 5% SDS polyacrylamide gels (Laemmli, U. K., Cleavage of structural proteins cluring the assembly of the head of bacteriophage T4, Nature 227, 680–685 (1970)). Gels with radioactive protein samples were impregnated in EN$^3$HANCE (Du Pont) before drying and exposure to film at -70° C. For Western analysis, gels were electroblotted onto Immobilon P membrane (Millipore), using semidry method (Biometra Fast Blot B33). Following electrophoresis the membranes were blocked with 3% milk powder in TBS buffer (25 mM Tris-HCl, pH 7.4, 137 mM NaCl, 2.7 mM KCl) followed by incubation with MARCO antiserum diluted 1:50–1:100 in TBS buffer. After washings with TBS buffer the membranes were incubated with alkaline-phosphatase-conjugated anti-rabbit IgG (Sigma), washed and developed with nitroblue tetrazolium/5-bromo-4-chloro-3-indolyl phosphate.

Cell Culture, Transfections and Metabolic Labeling

Cell lines IC-21 and COS-7 were from ATCC. IC-21 cells were grown in RPMI 1640 medium and COS-7 cells in high glucose (4.5 g/l) Dulbecco's Modified Eagle's medium (Gibco laboratories) both mediums were supplemented with 10% fetal calf serum, 2 mM L-glutamine, 100 IU/ml penicillin, and 75 mg/ml ascorbate. For cell transfections, a cDNA fragment containing the entire coding region of MARCO with the authentic translation initiation sequence was generated by oligonucleotide-primed polymerase chain reaction and its sequence was confirmed by DNA-sequencing. The product was cloned into the pSG5 expression vector (Green, S., Isseman, I., and Sheer, E., A versatile in vivo and in vitro eukaryotic expression vector for protein engineering, Nucl. Acid. Res. 16, 399 (1988)) using Bgl II restriction sites engineered into the primers. Additionally, a construct made with a 5'-PCR primer containing an additional consensus sequence GCCGCCACCATGG (Kozak, M, The scanning model for translation: An update. J. Cell. Biol. 108, 229–241 (1989)) was made for more effective initiation of translation. A construct containing the coding region in the opposite orientation (3'-5') was used as a control. A day before transfection, COS-7 cells were plated at $0.7 \times 10^6$ cells per 90 mm tissue culture dish. The cells were transfected overnight by the calcium phosphate method (Gorman, C., High efficiency gene transfer into mammalian cells. In DNA cloning, Volume II, A practical approach, D.M. Glover, ed (Oxford: IRL press), pp. 143–161 (1985)) using 20 μg DNA isolated with CsCl gradient centrifugation. After 18 hrs the calcium phosphate precipitate was removed, and cells used for immunostaining or binding assays were harvested with trypsin and replated.

For metabolic labeling cells were incubated for 1 hr or 4 hrs in methione-free DMEM medium containing 200 μCi/ml ($^{35}$S)methionine (Amersham >1000 Ci/mmol) and 10% dialysed FCS. The cells were then chased for 0, 3, 8 or 18 hrs in medium supplemented with unlabeled methionine. Following the pulse-chase label, the cells were washed with PBS buffer and then used in the immunoprecipitations. In N-glycosylation inhibition studies 3 mg/ml Tunicamycin was included in the medium 3 hrs before labeling and during the 4 hrs labeling period.

Studies of Ligands Binding to the MARCO Receptor and Inhibition of Binding with MARCO Antibodies For binding studies, IC-21 macrophages (positive control) and transfected COS cells cultured on coverslips were incubated in the culture medium at +37° C. with fluorescent labeled ligand candidates (Molecular Probes Inc); with FITC-labeled BioParticles, Escherichia coli, Staphylococcus aureus and Zymosan A (Saccharomyces cerevisiae) for 1 hour, and with DiI (1,1'-dioctadecyl-3,3,3',3'-tetramethyl-indocarbocyanine perchlorate)-labeled AcLDL (5 mg/ml) for 3–5 hrs. Bio Particles and cells were incubated in 50:1–100:1 ratios. In the Zymosan A binding studies higher particle amounts and longer incubation times were also tested. Following incubation the cells were rinsed five times with PBS solution, fixed with 4% paraformaldehyde or with ethanol for 10 minutes, and then immunostained using IgG against MARCO polypeptides and FITC- or rhodamine-labeled secondary antibodies as described in the immunofluorescence and confocal microscopy paragraph above. As negative controls, COS cells transfected with a plasmid containing cDNA in the wrong orientation were used.

Binding inhibition studies were carried out by adding normal rabbit IgG and MARCO anti-rabbit IgG (25–500 μg/ml) or preimmune and anti-MARCO sera at 1/10–1/100 dilutions prior to the addition of ligands. Bound bacteria were counted from one hundred cells positive with anti-MACRO antibodies, each experiment being carried out in triplicates.

B. RESULTS cDNA Clones and Deduced Primary Structure

Screening of a mouse macrophage cDNA library with a human type XIII collagen cDNA probe yielded several overlapping clones coding for a previously undescribed collagenous sequence. Screening of the same library with one of the cDNA inserts yielded new clones one of which, Maf-6, spanned a 1.8 kb sequence. This sequence contained an apparent 159 bp 5'-end untranslated region, a 1554 bp open reading frame, followed by over 156 bp 3'-end untranslated region containing a TGA translation stop codon, a putative AATAAA polyadenylation signal and a poly(A) tail (FIG. 2). The sequence surrounding the putative initiator methionine codon ATG does not agree completely with the Kozak consensus sequence, but it can be designated as strong translation initiation site when considering positions -3 and +4.

Analysis of the 1554 bp open reading frame predicted the sequence for a unique 518 residue polypeptide not existing in the data base (FIG. 2). The molecular weight of this polypeptide chain was calculated to be 52,738. The amino acid sequence indicated the presence of several distinct domains. The open reading frame starts with an ~50-residue hydrophilic domain I which starts with the initiator methionine and contains one cysteine. Therefore, this protein does not contain a hydrophobic signal peptide-like sequence characteristic for secreted proteins. Domain II has an ~25-residue hydrophobic sequence, which is followed by a hydrophilic domain III containing 75 residues, including two cysteine residues. Domain III also has two putative N-glycosylation sites (FIG. 2). The sequences of domain I, II and III are each unique, with no significant homology with sequences in the EMBL and Swiss protein data bases. Domain IV has a 270-residue collagenous sequence characterized by 89 Gly-Xaa-Yaa triplets interrupted at one location (residues 174–176) by the sequence Ala-Glu-Lys. The C-terminal globular domain V which has 99 residues, six of which are cysteine. The sequence of this domain showed 48.9% sequence identity with the C-terminal domain of scavenger receptor type I. With the exception of the collagenous domain IV, the other domains did not show significant homology with scavenger receptors or other known proteins.

Expression of MARCO

The initial cDNA clones for MARCO were isolated from a macrophage cDNA library. In order to obtain an overall picture of the spatial expression of MARCO, Northern analyses were first carried out with RNA isolated from several tissues, freshly isolated peritoneal macrophages and cultured cells. Using mRNA from adult mice, strong signals were observed with RNA from spleen and peritoneal macrophages, but not in other tissues, including liver (data not shown).

In situ hybridization was carried out on whole 14–17-day-old embryos and tissues from 2-month-old mice to assess more exactly which cells express MARCO in vivo. No signals above background were observed in the embryonic tissues (data not shown), but strong signals were seen with the MARCO antisense probe in a highly region-specific manner, both in spleen and lymph nodes (FIG. 4). In contrast, all other tissues examined, including lung and liver, which are rich in macrophages, did not show signals above background using the same probe (data not shown). The signals observed in the spleen were present in macrophage-like cells in the marginal zone at the interface of the white and red pulps (FIGS. 4A, B). In lymph nodes strong signals were seen in cells of the medullary region which is rich in macrophages (FIGS. 4G, H). Similar anlyses with a sense probe did not reveal positive signals in any of the tissues studied (not shown).

To examine if MARCO is expressed in established macrophage cell lines, applicants carried out Northern analysis with mRNA isolated from a cultured macrophage cell line IC-21 (ATCC TIB 186). These cells exhibited intense expression of an about 1.8 kb transcript (not shown).

Immunohistochemical localization of MARCO to Macrophages

In order to determine where the MARCO protein is located in vivo, antibodies were raised for immunohistological analyses. The putative extracellular globular domain V and intracellular domain I of the MARCO polypeptide chain were expressed as glutathione S-transferase (GST) fusion proteins in the pGEX-1λT vector in *E. coli* and then purified and used as antigens to raise antisera in rabbits. Immunostaining of frozen 2-month-old mouse spleen tissues revealed specific staining in macrophages located in the same region of the marginal zone (FIG. 4C) where we observed expression by in situ hybridization (FIGS. 4A, B). This indicates that MARCO is directly associated with the cells and not deposited into the extracellular matrix. Both antibodies gave identical results. No positive staining was observed in liver which is rich in scavenger receptor containing macrophages, indicating that the antibodies do not cross-react with the scavenger receptors.

Based on the immunohistochemical data a close relationship was observed in the spleen between the expression of MARCO and the marginal zone macrophage marker ER-TR9 (Dijkstra, C. D., Van Vliet, E., Döpp, E. A., Vander Lelij, A. A., and Kraal, G., Marginal zone macrophages identified by a monoclonal antibody: characterization of immuno- and enzyme-histochemical properties and functional capacities, *Immunology* 55, 23–28 (1985)). In the splenic marginal zone practically complete overlap was seen between the two macrophage markers (FIGS. 4C, D, E), and a similar correlation could be found for the expression of the two molecules in medullary macrophages in lymph nodes (not shown). As can be seen from FIG. 4, expression of MARCO and ER-TR9 was not present in the macrophages lining the marginal sinus which normally express the MOMA-1 antigen (FIG. 4F).

Immunohistological staining of lymph node tissue with both MARCO antibodies stained macrophages located in medullary cords (not shown) in accordance with the expression pattern obtained with the in situ hybridization riboprobe (FIGS. 4G, H). This correlates completely with the expression of ER-TR9 as previously reported (Dijkstra et al., 1985).

Immunolocalization and Orientation of MARCO on Macrophage Cell Surface

Cultured IC-21 transformed macrophages were processed for field emission scanning electron microscopy (FESEM) of the cell surface and reacted with antisera against the putative extracellular C-terminal or intracellular N-terminal domains followed by incubation with a gold-labeled second antibody. The antibody against the C-terminal domain V readily bound to the cell surface (FIGS. 5A and 5B), while the antibody against the N-terminal domain I did not (data not shown). The antibodies decorated the cell surface quite evenly and they also bound strongly to pseuodopodia which could protrude quite long distances from the cell membrane. Transmission immunoelectron microscopy revealed gold particles particularly associated with the plasma membranes, but also to some extent in intracellular membranes (not shown). Together, these results demonstrated that MARCO is a membrane protein, and that within the plasma membrane domain I is located intracellularly and domain V extracellularly.

In order to further examine the orientation of MARCO in the plasma membrane antisera against domains I or V were injected intravenously into mice, after which the tissues were processed, cryosectioned and analyzed for staining using an FITC-conjugated second antibody. In the spleen results revealed solely staining of marginal zone macrophages when the antiserum against domain V was used (FIG. 6), whereas no staining was observed in spleen sections of mice injected with the antiserum against domain I (data not shown). Other tissues such as liver were negative in this experiment. These results support the hypothesis that the N-terminal domain I and C-terminal domain V are intracellular and extracellular, respectively.

MARCO Polypeptide Chains Form Disulfide-linked Trimers in Vivo

The presence of a 270-residue long Gly-Xaa-Yaa-repeat containing sequence indicated that MARCO is a trimeric protein with a triple-helical domain similar to those in collagenous proteins. Furthermore, the presence of several cysteines in the polypeptide suggested that the chains might be disulfide-linked in such a trimer. In order to address this question, we extracted protein from intact mouse spleen and kidney (negative control) tissues, and carried out immunoprecipitation with the antibodies against domains I or V of MARCO, followed by immunoblotting (Sambrook, J., Fritsch, E. F., and Maniatis, T., Molecular Cloning: A laboratory Manual Second Edition. Cold Spring Harbor, N.Y., Cold Spring Harbor Laboratory Press (1989)) as described in Experimental Procedures. This study revealed that when the spleen extract was immunoprecipitated, electrophoresed on a 5% gel without reduction an immunoblotted, a major band of about 210,000 daltons and a second slightly smaller, weaker band, were seen with both antibodies (FIG. 7A lanes 1 and 2). A broad band of about 160,000 daltons representing IgG was also present. These bands disappeared when the samples were electrophoresed after reduction, while one diffuse major band of about 80,000 daltons and one weaker, slightly smaller band appeared (FIG. 7A lane 5). In addition, a strong 50,000 dalton band representing IgG was present. No specific protein was precipitated from the kidney extract with the MARCO antibodies (FIG. 7A, lanes 3, 4 and 6). These results strongly suggest that the MARCO molecule has a trimeric conformation containing interchain disulfide bonds. The nature of the weaker, smaller bands is not sure, but since they were recognized by both antibodies, they might represent forms with different posttranslational modifications.

Characterization of MARCO by Metabolic Labeling of Transfected COS Cells

COS cells, which normally do not express MARCO, were transfected with full-length cDNA to study glycosylation of the chains and also if native MARCO trimers can be formed with a single type of chains. Furthermore, labeling studies were carried out in the presence of Tunicamycin in order to examine if the minor heterogeneity of specifically immunoprecipitated bands might be due to differences in degree of glycosylation. Incubation with Tunicamycin, which inhibits N-glycosylation, revealed a MARCO chain with a size of ~50,000 daltons which agrees well with the calculated size based on the amino acid sequence predicted from the cDNA (FIG. 7B, lane 5). In pulse-chase experiments, cells were first pulsed for 1 or 4 hours and the label was then chased for up to 18 hours. After the pulse the major band had a size of about 60,000 daltons, but additional specifically immunoprecipitated bands had sizes of up to 80,000 daltons after reduction (FIG. 7B, lane 3). After 18 hours chase the 60,000 dalton bands had disappeared, but two bands of 70,000 daltons and a doublet of about 80,000 remained (FIG. 7B, lane 4). These results suggest that the microheterogeneity of sizes of the subunit chains of MARCO is due to differences in glycosylation, but not proteolysis as these proteins were detected with antibodies reacting with both ends of the polypeptide (data not shown).

Pulse-labeled immunoprecipitated MARCO extracted from the transfected cells was electrophoresed on SDS-PAGE without reduction and compared with MARCO immunoprecipitated from a spleen tissue extract. The results showed that the sizes of trimeric MARCO proteins from the COS cells (FIG. 9B, lane 1) and spleen (FIG. 7A, lanes 1 and 2) corresponded to each other. COS cells transfected with a construct containing MARCO cDNA in the wrong orientation did not reveal specific bands after immunoprecipitation (FIG. 7B, lanes 2 and 6). Together, the labeling data demonstrated that the transfected cells were able to synthesize single MARCO chains and assemble them into disulfide-bonded homotrimers.

Studies on Binding Properties of MARCO

The marginal zone macrophages in the spleen have been proposed to play a key role in the host-defense system by recognizing and phagocytosing blood pathogens such as bacteria and yeast. For example, the cells can selectively take up neutral polysaccharides present on bacterial walls. To initially characterize the potential binding properties of MARCO, cultured transfected CoS cells, and IC-21 macrophages used as positive control cells, were incubated with several fluorescein-labeled bioprobes. When transfected COS cells expressing MARCO were incubated with labeled *E. coli* and *S. aureus* bacteria, specific binding was seen to cells which were immunopositive with MARCO antibodies (FIGS. 8 A,B). In contrast, labeled S. cerevisiae (Zymosan A) did not bind to COS cells expressing MARCO (FIG. 8C). Cultured IC-21 macrophages bound all three probes (FIGS. 8D–F). As negative control, COS cells transfected with a plasmid containing MARCO cDNA in the wrong orientation did not bind any of the probes (not shown).

The binding of *S. aureus* could be inhibited efficiently by antiserum (not shown) and IgG (FIG. 9) raised against domains IV and V. Binding of *E. coli* could also be inhibited by these antibodies (not shown).

Due to the structural homology of MARCO with macrophage scavenger receptors which bind a variety of ligands such as acetylated LDL, we also investigated if MARCO cDNA transfected COS cells bind this compound. The results showed that MARCO expressing COS cells readily bound DiI-acetylated LDL (FIG. 10).

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH:        1868 base pairs
        (B) TYPE:          Nucleic acid
        (C) STRANDEDNESS:  Single
        (D) TOPOLOGY:      Linear (ii) MOLECULE TYPE:      Nucleotide-genomic DNA (iii) HYPOTHETICAL:      Not relevant (iv) ANTI-SENSE:        Not relevant (x) SEQUENCE DESCRIPTION: SEQ ID NO:1:

```
TCCCCACAG CCAGGAAACA TTGTGCAAAT TGAAAAATCA                                39

TTGCCAAAGG GAAGTTGTAT GCATCTCCAG CTAGCTGCCG CAGTTAAATG GGAGCCCTGC        99

TTCCTCCTAG GGGAGAGTTT CTGCTGGCTC CAGGGCTTTG GCCACCTATA AAGCTTAGCA       159

ATG GGA AGT AAA GAA CTC CTC AAA GAG GAA GAC TTC TTG GGC AGC ACA         207
MET GLY SER LYS GLU LEU LEU LYS GLU GLU ASP PHE LEU GLY SER THR
1               5                   10                  15

GAA GAC AGA GCC GAT TTT GAC CAA GCT ATG TTC CCT GTG ATG GAG ACC         255
GLU ASP ARG ALA ASP PHE ASP GLN ALA MET PHE PRO VAL MET GLU THR
            20                  25                  30

TTC GAA ATC AAT GAT CCA GTG CCC AAG AAG AGA AAT GGG GGG ACC TTC         303
PHE GLU ILE ASN ASP PRO VAL PRO LYS LYS ARG ASN GLY GLY THR PHE
        35                  40                  45

TGC ATG GCA GTC ATG GCC ATC CAC CTG ATC CTG CTC ACG GCA GGT ACT         351
CYS MET ALA VAL MET ALA ILE HIS LEU ILE LEU LEU THR ALA GLY THR
    50                  55                  60

GCA CTG CTG CTG ATT CAA GTT CTC AAT CTG CAG GAG CAG CTC CAG ATG         399
ALA LEU LEU LEU ILE GLN VAL LEU ASN LEU GLN GLU GLN LEU GLN MET
65                  70                  75                  80

CTA GAG ATG TGC TGT GGC AAT GGA TCA CTA GCT ATC GAG GAC AAG CCC         447
LEU GLU MET CYS CYS GLY ASN GLY SER LEU ALA ILE GLU ASP LYS PRO
                85                  90                  95

TTC TTC TCG CTG CAG TGG GCA CCC AAA ACA CAC CTG GTA CCT AGA GCA         495
PHE PHE SER LEU GLN TRP ALA PRO LYS THR HIS LEU VAL PRO ARG ALA
            100                 105                 110

CAG GGG CTG CAA GCC TTG CAG GCC CAG CTC AGC TGG GTC CAT ACC AGC         543
GLN GLY LEU GLN ALA LEU GLN ALA GLN LEU SER TRP VAL HIS THR SER
        115                 120                 125

CAG GAG CAA CTC CGT CAG CAG TTC AAC AAC CTC ACT CAA AAT CCA GAG         591
GLN GLU GLN LEU ARG GLN GLN PHE ASN ASN LEU THR GLN ASN PRO GLU
    130                 135                 140

TTG TTC CAG ATT AAA GGT GAA CGA GGC TCT CCA GGT CCA AAA GGG GCC         639
LEU PHE GLN ILE LYS GLY GLU ARG GLY SER PRO GLY PRO LYS GLY ALA
145                 150                 155                 160

CCG GGT GCT CCT GGA ATC CCC GGG CTG CCT GGG CCA GCT GCT GAG AAG         687
PRO GLY ALA PRO GLY ILE PRO GLY LEU PRO GLY PRO ALA ALA GLU LYS
                165                 170                 175

GGA GAA AAG GGG GCT GCA GGT CGT GAT GGA ACC CCA GGT GTC CAA GGA         735
GLY GLU LYS GLY ALA ALA GLY ARG ASP GLY THR PRO GLY VAL GLN GLY
            180                 185                 190

CCC CAG GGC CCA CCA GGC AGC AAG GGA GAG GCA GGC CTC CAG GGA CTT         783
PRO GLN GLY PRO PRO GLY SER LYS GLY GLU ALA GLY LEU GLN GLY LEU
        195                 200                 205

ACG GGT GCA CCA GGG AAG CAA GGA GCA ACT GGT GCT CCA GGA CCT CGA         831
THR GLY ALA PRO GLY LYS GLN GLY ALA THR GLY ALA PRO GLY PRO ARG
    210                 215                 220

GGA GAG AAG GGC AGC AAA GGT GAC ATA GGT CTC ACT GGC CCC AAG GGG         879
GLY GLU LYS GLY SER LYS GLY ASP ILE GLY LEU THR GLY PRO LYS GLY
225                 230                 235                 240

GAA CAT GGC ACC AAG GGA GAC AAA GGG GAC CTA GGC CTT CCA GGA AAC         927
GLU HIS GLY THR LYS GLY ASP LYS GLY ASP LEU GLY LEU PRO GLY ASN
                245                 250                 255

AAA GGG GAC ATG GGC ATG AAG GGA GAC ACG GGG CCC ATG GGG TCC CCT         975
LYS GLY ASP MET GLY MET LYS GLY ASP THR GLY PRO MET GLY SER PRO
            260                 265                 270

GGA GCT CAG GGA GGT AAA GGT GAT GCT GGA AAA CCA GGC CTA CCA GGT        1023
GLY ALA GLN GLY GLY LYS GLY ASP ALA GLY LYS PRO GLY LEU PRO GLY
        275                 280                 285

TTG GCT GGA TCT CCA GGA GTC AAA GGT GAC CAA GGA AAA CCT GGA GTG        1071
```

```
LEU ALA GLY SER PRO GLY VAL LYS GLY ASP GLN GLY LYS PRO GLY VAL
    290                 295                 300

CAG GGT GTT CCA GGC CCT CAA GGT GCA CCA GGA CTT TCA GGT GCC AAG    1119
GLN GLY VAL PRO GLY PRO GLN GLY ALA PRO GLY LEU SER GLY ALA LYS
305                 310                 315                 320

GGT GAG CCA GGA CGC ACT GGT CTT CCT GGG CCA GCA GGA CCC CCG GGA    1167
GLY GLU PRO GLY ARG THR GLY LEU PRO GLY PRO ALA GLY PRO PRO GLY
                325                 330                 335

ATT GCT GGG AAT CCA GGG ATT GCA GGT GTG AAA GGA AGC AAG GGT GAC    1215
ILE ALA GLY ASN PRO GLY ILE ALA GLY VAL LYS GLY SER LYS GLY ASP
            340                 345                 350

ACA GGA ATT CAA GGA CAG AAA GGC ACA AAA GGA GAA TCA GGA GTC CCA    1263
THR GLY ILE GLN GLY GLN LYS GLY THR LYS GLY GLU SER GLY VAL PRO
                355                 360                 365

GGT CTT GTA GGC AGA AAG GGA GAC ACT GGA AGC CCT GGG CTG GCA GGT    1311
GLY LEU VAL GLY ARG LYS GLY ASP THR GLY SER PRO GLY LEU ALA GLY
    370                 375                 380

CCC AAA GGA GAA CCT GGA CGA GTC GGT CAG AAG GGA GAC CCG GGG ATG    1359
PRO LYS GLY GLU PRO GLY ARG VAL GLY GLN LYS GLY ASP PRO GLY MET
385                 390                 395                 400

AAA GGG TCT TCT GGC CAG CAA GGA CAA AAG GGA GAA AAG GGT CAA AAA    1407
LYS GLY SER SER GLY GLN GLN GLY GLN LYS GLY GLU LYS GLY GLN LYS
                405                 410                 415

GGC GAA TCT TTC CAA CGC GTC CGG ATC ATG GGT GGC ACC AAC AGA GGC    1455
GLY GLU SER PHE GLN ARG VAL ARG ILE MET GLY GLY THR ASN ARG GLY
            420                 425                 430

CGA GCT GAA GTT TAC TAT AAC AAT GAG TGG GGG ACA ATT TGT GAT GAT    1503
ARG ALA GLU VAL TYR TYR ASN ASN GLU TRP GLY THR ILE CYS ASP ASP
                435                 440                 445

GAT TGG GAT AAT AAT GAT GCG ACT GTC TTC TGT CGC ATG CTC GGT TAC    1551
ASP TRP ASP ASN ASN ASP ALA THR VAL PHE CYS ARG MET LEU GLY TYR
    450                 455                 460

TCC AGA GGG AGA GCA CTT AGC AGC TAT GGA GGT GGC TCT GGG AAC ATC    1599
SER ARG GLY ARG ALA LEU SER SER TYR GLY GLY GLY SER GLY ASN ILE
465                 470                 475                 480

TGG CTG GAC AAT GTG AAT TGT CGG GGC ACA GAG AAC AGT TTG TGG GAC    1647
TRP LEU ASP ASN VAL ASN CYS ARG GLY THR GLU ASN SER LEU TRP ASP
                485                 490                 495

TGC AGT AAG AAC TCC TGG GGC AAT CAC AAT TGC GTA CAT AAT GAA GAT    1695
CYS SER LYS ASN SER TRP GLY ASN HIS ASN CYS VAL HIS ASN GLU ASP
            500                 505                 510

GCG GGT GTG GAA TGC TCC TGA  CTT GGGAGCCCGA GAGGTCATCA GTGTGTCCCC  1749
ALA GLY VAL GLU CYS SER
                515

AGGTGTCTTT GGTTCCACCC ACATGGAAAT CTGTGGGCTT GCCAACTCTG TTGAGGGGAA  1809

GTTAATAAAG CTCAAGTGGG GATCTGAAAA AAAAAAAAA AAAAAAAAAA AAAAAAAA     1868

(2) INFORMATION FOR SEQ ID NO:2:

(i) SEQUENCE CHARACTERISTICS:
         (A) LENGTH:    518 amino acids
         (B) TYPE: amino acid
         (C) STRANDEDNESS:  Single
         (D) TOPOLOGY: Linear (x) SEQUENCE DESCRIPTION: SEQ ID NO:2:

Met Gly Ser Lys Glu Leu Leu Lys Glu Glu Asp Phe
 1               5                  10

Leu Gly Ser Thr Glu Asp Arg Ala Asp Phe Asp Gln
            15                  20
```

```
Ala Met Phe Pro Val Met Glu Thr Phe Glu Ile Asn
 25                  30                  35

Asp Pro Val Pro Lys Lys Arg Asn Gly Gly Thr Phe
             40                  45

Cys Met Ala Val Met Ala Ile His Leu Ile Leu Leu
 50                  55                       60

Thr Ala Gly Thr Ala Leu Leu Leu Ile Gln Val Leu
                 65                  70

Asn Leu Gln Glu Gln Leu Gln Met Leu Glu Met Cys
         75                  80

Cys Gly Asn Gly Ser Leu Ala Ile Glu Asp Lys Pro
 85                  90                  95

Phe Phe Ser Leu Gln Trp Ala Pro Lys Thr His Leu
            100                 105

Val Pro Arg Ala Gln Gly Leu Gln Ala Leu Gln Ala
        110                 115                 120

Gln Leu Ser Trp Val His Thr Ser Gln Glu Gln Leu
                125                 130

Arg Gln Gln Phe Asn Asn Leu Thr Gln Asn Pro Glu
        135                 140

Leu Phe Gln Ile Lys Gly Glu Arg Gly Ser Pro Gly
145                 150                 155

Pro Lys Gly Ala Pro Gly Ala Pro Gly Ile Pro Gly
            160                 165

Leu Pro Gly Pro Ala Ala Glu Lys Gly Glu Lys Gly
    170                 175                 180

Ala Ala Gly Arg Asp Gly Thr Pro Gly Val Gln Gly
            185                 190

Pro Gln Gly Pro Pro Gly Ser Lys Gly Glu Ala Gly
        195                 200

Leu Gln Gly Leu Thr Gly Ala Pro Gly Lys Gln Gly
205                 210                 215

Ala Thr Gly Ala Pro Gly Pro Arg Gly Glu Lys Gly
            220                 225

Ser Lys Gly Asp Ile Gly Leu Thr Gly Pro Lys Gly
230                 235                 240

Glu His Gly Thr Lys Gly Asp Lys Gly Asp Leu Gly
            245                 250

Leu Pro Gly Asn Lys Gly Asp Met Gly Met Lys Gly
        255                 260

Asp Thr Gly Pro Met Gly Ser Pro Gly Ala Gln Gly
265                 270                 275

Gly Lys Gly Asp Ala Gly Lys Pro Gly Leu Pro Gly
            280                 285

Leu Ala Gly Ser Pro Gly Val Lys Gly Asp Gln Gly
    290                 295                 300

Lys Pro Gly Val Gln Gly Val Pro Gly Pro Gln Gly
                305                 310

Ala Pro Gly Leu Ser Gly Ala Lys Gly Glu Pro Gly
            315                 320

Arg Thr Gly Leu Pro Gly Ala Gly Pro Pro Gly
325                 330                 335

Ile Ala Gly Asn Pro Gly Ile Ala Gly Val Lys Gly
            340                 345
```

```
Ser Lys Gly Asp Thr Gly Ile Gln Gly Gln Lys Gly
    350             355             360

Thr Lys Gly Glu Ser Gly Val Pro Gly Leu Val Gly
            365             370

Arg Lys Gly Asp Thr Gly Ser Pro Gly Leu Ala Gly
        375             380

Pro Lys Gly Glu Pro Gly Arg Val Gly Gln Lys Gly
385             390             395

Asp Pro Gly Met Lys Gly Ser Ser Gly Gln Gln Gly
            400             405

Gln Lys Gly Glu Lys Gly Gln Lys Gly Glu Ser Phe
    410             415             420

Gln Arg Val Arg Ile Met Gly Gly Thr Asn Arg Gly
                425             430

Arg Ala Glu Val Tyr Tyr Asn Asn Glu Trp Gly Thr
        435             440

Ile Cys Asp Asp Asp Trp Asp Asn Asn Asp Ala Thr
445             450             455

Val Phe Cys Arg Met Leu Gly Tyr Ser Arg Gly Arg
            460             465

Ala Leu Ser Ser Tyr Gly Gly Gly Ser Gly Asn Ile
    470             475             480

Trp Leu Asp Asn Val Asn Cys Arg Gly Thr Glu Asn
            485             490

Ser Leu Trp Asp Cys Ser Lys Asn Ser Trp Gly Asn
        495             500

His Asn Cys Val His Asn Glu Asp Ala Gly Val Glu
505             510             515

Cys Se
```

Having thus described the invention, it is claimed:

1. An isolated murine plasma membrane associated polypeptide expressed postnatally by a subpopulation of macrophages, comprising the polypeptide (SEQ. ID NO. 2) identified in FIG. 2.

2. The isolated murine plasma membrane associated polypeptide of claim 1, wherein said polypeptide is 518 amino acids in length.

3. The isolated murine plasma membrane associated polypeptide of claim 1, wherein said polypeptide is about 52,738 Daltons in molecular weight.

4. The isolated murine plasma membrane associated polypeptide of claim 1, wherein said polypeptide is expressed in subpopulations of macrophages in the spleen, lymph nodes and the peritoneum.

5. The isolated macrophage receptor of claim 1, wherein said receptor binds both gram positive and gram negative bacteria and acetylated LDL, but not yeast.

* * * * *